US010105456B2

(12) United States Patent
Harmsen et al.

(10) Patent No.: US 10,105,456 B2
(45) Date of Patent: Oct. 23, 2018

(54) MULTIMODAL PARTICLES, METHODS AND USES THEREOF

(71) Applicant: SLOAN-KETTERING INSTITUTE FOR CANCER RESEARCH, New York, NY (US)

(72) Inventors: Stefan Harmsen, New York, NY (US); Matthew Wall, New York, NY (US); Moritz Kircher, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 147 days.

(21) Appl. No.: 14/653,177

(22) PCT Filed: Dec. 19, 2013

(86) PCT No.: PCT/US2013/076475
§ 371 (c)(1),
(2) Date: Jun. 17, 2015

(87) PCT Pub. No.: WO2014/100380
PCT Pub. Date: Jun. 26, 2014

(65) Prior Publication Data
US 2015/0328346 A1 Nov. 19, 2015

Related U.S. Application Data

(60) Provisional application No. 61/739,556, filed on Dec. 19, 2012.

(51) Int. Cl.
*A61K 49/00* (2006.01)
*A61K 49/18* (2006.01)
*A61K 51/12* (2006.01)

(52) U.S. Cl.
CPC ...... *A61K 49/0093* (2013.01); *A61K 49/1824* (2013.01); *A61K 51/1244* (2013.01)

(58) Field of Classification Search
CPC combination set(s) only.
See application file for complete search history.

(56) References Cited

U.S. PATENT DOCUMENTS

| | | |
|---|---|---|
| 4,604,992 A | 8/1986 | Sato |
| 4,669,467 A | 6/1987 | Willett et al. |
| 4,938,205 A | 7/1990 | Nudelman |
| 5,275,594 A | 1/1994 | Baker et al. |
| 5,293,872 A | 3/1994 | Alfano et al. |
| 5,300,097 A | 4/1994 | Lerner et al. |
| 5,306,403 A | 4/1994 | Vo-Dinh |
| 5,594,497 A | 1/1997 | Ahern et al. |
| 5,609,907 A | 3/1997 | Natan |
| 5,713,364 A | 2/1998 | DeBaryshe et al. |
| 5,721,102 A | 2/1998 | Vo-Dinh |
| 5,813,987 A | 9/1998 | Modell et al. |
| 6,002,471 A | 12/1999 | Quake |
| 6,008,889 A | 12/1999 | Zeng et al. |
| 6,019,719 A | 2/2000 | Schulz et al. |
| 6,025,202 A | 2/2000 | Natan |
| 6,127,120 A | 10/2000 | Graham et al. |
| 6,174,291 B1 | 1/2001 | McMahon et al. |
| 6,174,677 B1 | 1/2001 | Vo-Dinh |
| 6,219,137 B1 | 4/2001 | Vo-Dinh |
| 6,242,264 B1 | 6/2001 | Natan et al. |
| 6,251,127 B1 | 6/2001 | Biel |
| 6,254,852 B1 | 7/2001 | Glajch et al. |
| 6,514,767 B1 | 2/2003 | Natan |
| 6,579,726 B1 | 6/2003 | Natan et al. |
| 6,624,886 B2 | 9/2003 | Natan et al. |
| 6,640,130 B1 | 10/2003 | Freeman et al. |
| 6,959,024 B2 | 10/2005 | Paldus et al. |
| 7,076,092 B2 | 7/2006 | Hollars et al. |

(Continued)

FOREIGN PATENT DOCUMENTS

| | | |
|---|---|---|
| CN | 101679022 A | 3/2010 |
| CN | 102015020 A | 4/2011 |

(Continued)

OTHER PUBLICATIONS

Fales et al., Langmuir, Oct. 4, 2011; 27(19):12186-12190.*
International Search Report, PCT/US2015/045646, dated Nov. 27, 2015, 5 pages.
Written Opinion, PCT/US2015/045646, dated Nov. 27, 2015, 7 pages.
Adiseshaiah, P.P. et al., Nanomaterial standards for efficacy and toxicity assessment, Advanced Review, 2:99-112 (2009).
Agarwal, A. et al., Targeted gold nanorod contrast agent for prostate cancer detection by photoacoustic imaging, Journal of Applied Physics, 102:064701-064704 (2007).
Aggarwal, S. et al., What's fueling the biotech engine—2009-2010, Nature Biotechnology, 28(11):1165-1171 (2010).
Beljebbar, A. et al., Ex vivo and in vivo diagnosis of C6 glioblastoma development by Raman spectroscopy coupled to a microprobe, Anal Bioanal Chem, 398:477-487 (2010).

(Continued)

*Primary Examiner* — Robert S Cabral
(74) *Attorney, Agent, or Firm* — Brenda Herschbach Jarrell; Su Kyung Suh; Choate, Hall & Stewart LLP

(57) ABSTRACT

The present disclosure, among other things, provides a composition of a particle including a substrate; at least a first condensation layer comprising at least a first dopant entity; and at least a second layer comprising a second dopant entity. In some embodiments, different dopant entities are included in different layers. In some embodiments, such dopant entities are or comprise detectable entities. This, in some embodiments, provided technologies achieve multimodality particles. Among the many advantages of provided technologies include the ability to image particles by a plurality of distinct imaging modalities and/or in a plurality of contexts (e.g., pre-surgical, intraoperative and/or post-surgical environments). The present invention provides methods that include a single administration of particles to a subject, followed by a plurality of steps that comprise imaging the administered particles, which steps may utilize different imaging technologies and/or be performed at different times and/or in different environments.

29 Claims, 19 Drawing Sheets

(56) References Cited

U.S. PATENT DOCUMENTS

| | | |
|---|---|---|
| 7,192,778 B2 | 3/2007 | Natan |
| 7,443,489 B2 | 10/2008 | Natan |
| 7,538,859 B2 | 5/2009 | Tearney et al. |
| 7,656,525 B2 | 2/2010 | Zhao et al. |
| 7,738,096 B2 | 6/2010 | Zhao et al. |
| 7,760,352 B2 | 7/2010 | Armstrong et al. |
| 7,826,176 B2 | 11/2010 | Shirotori et al. |
| 7,829,140 B1 | 11/2010 | Zhong et al. |
| 8,054,463 B2 | 11/2011 | Morris et al. |
| 8,409,862 B2 | 4/2013 | Caulfield et al. |
| 8,409,863 B2 | 4/2013 | Natan et al. |
| 8,497,131 B2 | 7/2013 | Natan et al. |
| 8,568,878 B2 | 10/2013 | Wilson et al. |
| 8,795,628 B2 | 8/2014 | Gambhir et al. |
| 8,918,161 B2 | 12/2014 | Natan et al. |
| 9,295,391 B1 | 3/2016 | Tearney et al. |
| 2002/0165594 A1 | 11/2002 | Biel |
| 2003/0055307 A1 | 3/2003 | Elmaleh et al. |
| 2003/0191379 A1 | 10/2003 | Benaron et al. |
| 2004/0009341 A1 | 1/2004 | Naasani |
| 2004/0010192 A1 | 1/2004 | Benaron et al. |
| 2004/0073120 A1 | 4/2004 | Motz et al. |
| 2004/0225222 A1 | 11/2004 | Zeng et al. |
| 2004/0254419 A1 | 12/2004 | Wang et al. |
| 2004/0254454 A1 | 12/2004 | Kockro |
| 2005/0014851 A1 | 1/2005 | Bringley |
| 2005/0074779 A1 | 4/2005 | Vo-Dinh |
| 2005/0143662 A1 | 6/2005 | Marchitto et al. |
| 2005/0221494 A1 | 10/2005 | Natan |
| 2005/0272160 A1 | 12/2005 | Natan |
| 2006/0008924 A1 | 1/2006 | Anker et al. |
| 2006/0054506 A1 | 3/2006 | Natan et al. |
| 2007/0010809 A1 | 1/2007 | Hovda et al. |
| 2007/0134805 A1 | 6/2007 | Gilbert |
| 2007/0167838 A1 | 7/2007 | Hubble et al. |
| 2007/0178067 A1 | 8/2007 | Maier et al. |
| 2007/0232874 A1 | 10/2007 | Ince |
| 2007/0238953 A1 | 10/2007 | Lucassen et al. |
| 2007/0255356 A1 | 11/2007 | Rose et al. |
| 2007/0260295 A1 | 11/2007 | Chen et al. |
| 2007/0269382 A1 | 11/2007 | Santra et al. |
| 2007/0282190 A1 | 12/2007 | Dekel et al. |
| 2008/0007716 A1 | 1/2008 | Igarashi |
| 2008/0058908 A1 | 3/2008 | Bornstein |
| 2008/0089839 A1 | 4/2008 | Lu et al. |
| 2008/0095852 A1 | 4/2008 | Kong et al. |
| 2008/0118912 A1 | 5/2008 | Dickson et al. |
| 2008/0119832 A1 | 5/2008 | Cronin |
| 2008/0305045 A1 | 12/2008 | Kuniyil et al. |
| 2009/0137666 A1 | 5/2009 | Wang et al. |
| 2009/0171330 A1 | 7/2009 | Taylor et al. |
| 2009/0204111 A1 | 8/2009 | Bissig et al. |
| 2009/0218550 A1 | 9/2009 | Koyakutty et al. |
| 2009/0237648 A1 | 9/2009 | Armstrong et al. |
| 2009/0263485 A1 | 10/2009 | Li et al. |
| 2009/0281536 A1 | 11/2009 | Beckman et al. |
| 2009/0285766 A1 | 11/2009 | Kishen et al. |
| 2009/0294692 A1 | 12/2009 | Bourke, Jr. et al. |
| 2009/0304581 A1 | 12/2009 | Scheinberg et al. |
| 2010/0016783 A1 | 1/2010 | Bourke, Jr. et al. |
| 2010/0045778 A1 | 2/2010 | Yelin |
| 2010/0166650 A1 | 7/2010 | Gambhir |
| 2010/0197937 A1 | 8/2010 | Minami et al. |
| 2010/0211137 A1 | 8/2010 | Kim et al. |
| 2010/0279272 A1* | 11/2010 | Burrell ............... G01N 21/658 435/5 |
| 2011/0021970 A1 | 1/2011 | Vo-Dinh et al. |
| 2011/0152692 A1 | 6/2011 | Nie et al. |
| 2011/0165077 A1 | 7/2011 | Qian et al. |
| 2011/0182881 A1 | 7/2011 | Chin et al. |
| 2011/0190760 A1 | 8/2011 | Niver et al. |
| 2011/0207231 A1 | 8/2011 | Natan et al. |
| 2011/0230760 A1 | 9/2011 | Gambhir et al. |
| 2011/0262351 A1 | 10/2011 | Chung et al. |
| 2011/0263920 A1 | 10/2011 | Bourke, Jr. et al. |
| 2011/0282181 A1 | 11/2011 | Wang et al. |
| 2012/0123205 A1 | 5/2012 | Nie et al. |
| 2012/0136241 A1 | 5/2012 | Chen et al. |
| 2012/0141981 A1 | 6/2012 | Pantazis et al. |
| 2012/0164624 A1 | 6/2012 | Natan et al. |
| 2012/0179029 A1 | 7/2012 | Kircher et al. |
| 2012/0212733 A1 | 8/2012 | Kodali et al. |
| 2012/0226139 A1 | 9/2012 | Peyman |
| 2012/0251450 A1* | 10/2012 | Punnoose ............... A61K 33/08 424/9.1 |
| 2012/0282632 A1 | 11/2012 | Chiu et al. |
| 2012/0283379 A1 | 11/2012 | Auger et al. |
| 2012/0302940 A1 | 11/2012 | Ray |
| 2013/0012794 A1 | 1/2013 | Zeng et al. |
| 2013/0023770 A1 | 1/2013 | Courtney et al. |
| 2013/0029360 A1 | 1/2013 | Suh et al. |
| 2013/0040292 A1 | 2/2013 | Fernandez Lopez et al. |
| 2013/0330839 A1 | 12/2013 | Suh et al. |
| 2014/0316255 A1 | 10/2014 | Garai et al. |
| 2014/0350534 A1 | 11/2014 | Kircher et al. |
| 2015/0018807 A1 | 1/2015 | Kircher et al. |
| 2015/0258218 A1 | 9/2015 | Kircher et al. |
| 2016/0000329 A1 | 1/2016 | Kircher et al. |

FOREIGN PATENT DOCUMENTS

| | | |
|---|---|---|
| CN | 102175655 A | 9/2011 |
| CN | 102410994 A | 4/2012 |
| CN | 102686181 A | 9/2012 |
| CN | 102770071 A | 11/2012 |
| CN | 102559190 B | 9/2013 |
| DE | 102 49 674 A1 | 5/2004 |
| DE | 10 2011 103 950 A1 | 12/2012 |
| JP | H09-005666 A | 1/1997 |
| JP | H11-084307 A | 3/1999 |
| JP | 2003/503135 A | 1/2003 |
| JP | 2004/193545 A | 7/2004 |
| JP | 2005 306827 A | 11/2005 |
| JP | 2009/011546 A | 1/2009 |
| JP | 2009/508571 A | 3/2009 |
| JP | 2009/511891 A | 3/2009 |
| JP | 2009/222713 A | 10/2009 |
| JP | 2010/523983 A | 7/2010 |
| TW | 572748 B | 1/2004 |
| WO | WO-90/03803 A1 | 4/1990 |
| WO | WO-93/03672 A1 | 3/1993 |
| WO | WO-00/41611 A2 | 7/2000 |
| WO | WO-01/01854 A2 | 1/2001 |
| WO | WO-02/100285 A1 | 12/2002 |
| WO | WO-2005/107623 A2 | 11/2005 |
| WO | WO2008/122035 | 10/2008 |
| WO | WO-2010/096828 A1 | 8/2010 |
| WO | WO-2010/111066 A2 | 9/2010 |
| WO | WO-2011/025640 A1 | 3/2011 |
| WO | WO-2011/084528 A1 | 7/2011 |
| WO | WO-2012/065163 A2 | 5/2012 |
| WO | WO-2014/036470 A1 | 3/2014 |
| WO | WO-2014/089247 A2 | 6/2014 |
| WO | WO-2014/100380 A2 | 6/2014 |
| WO | WO-2014/130736 A1 | 8/2014 |
| WO | WO-2016/028749 A1 | 2/2016 |

OTHER PUBLICATIONS

Binkley, J. et al., RNA ligands to human nerve growth factor, Nucleic Acids Research, 23(16):3198-3205 (1995).

Bucci, M.K. et al., Near Complete Surgical Resection Predicts a Favorable Outcome in Pediatric Patients with Nonbrainstem, Malignant Gliomas, Cancer, 101(4): 817-824 (2004).

De La Zerda, A. et al., A Comparison Between Time Domain and Spectral Imaging Systems for Imaging Quantum Dots in Small Living Animals, Molecular Imaging and Biology, 12:500-508 (2010).

De La Zerda, A. et al., Advanced contrast nanoagents for photoacoustic molecular imaging, cytometry, blood test and photothermal theranostics, Contrast Media Mol. Imaging, 6:346-369 (2011).

De La Zerda, A. et al., Carbon nanotubes as photoacoustic molecular imaging agents in living mice, Letters, Nature Nanotechnology, 3:557-562 (2008).

(56) References Cited

OTHER PUBLICATIONS

De La Zerda, A. et al., Ultrahigh Sensitivity Carbon Nanotube Agents for Photoacoustic Molecular Imaging in Living Mice, Nano Letters, 10:2168-2172 (2010).
Eghtedari, M. et al., High Sensitivity of In Vivo Detection of Gold Nanorods Using a Laser Optoacoustic Imaging System, Nano Letters, 7(7):1914-1918 (2007).
Ermilov, S.A. et al., Laser optoacoustic imaging system for detection of breast cancer, Journal of Biomedical Optics, 14(2):024007-1-14 (2009).
Haaland, D.M. and Easterling, R.G., Improved Sensitivity of Infrared Spectroscopy by the Application of Least Squares Methods, Applied Spectroscopy, 34(5):539-548 (1980).
Harmsen, S. et al., Surface-enhanced resonance Raman scattering nanostars for high-precision cancer imaging, Science Translational Medicine, 7(271):1-8 (2015).
International Preliminary Report on Patentability, Application No. PCT/US13/57636, dated Aug. 1, 2014, 27 pages.
International Search Report, PCT/US2013/057636, dated Jan. 3, 2014, 3 pages.
International Search Report, PCT/US2013/076475, dated Jun. 16, 2014, 4 pages.
International Search Report, PCT/US2014/017508, dated May 12, 2014, 3 pages.
Jellinek, D.J. et al., Inhibition of Receptor Binding by High-Affinity RNA Ligands to Vascular Endothelial Growth Factor, Biochemistry, 33:10450-10456 (1994).
Kantelhardt, S.R. et al., Multiphoton Excitation Fluorescence Microscopy of 5-Aminolevulinic Acid Induced Fluorescence in Experimental Gliomas, Laser in Surgery and Medicine, 40:273-281 (2008).
Keren, S. et al., Noninvasive molecular imaging of small living subjects using Raman spectroscopy, PNAS, 105(15):5844-5849 (2008).
Kim, G. et al., Indocyanine-green-embedded PEBBLEs as a contrast agent of photoacoustic imaging, Journal of Biomedical Optics, 12(4):044020-1-8 (2007).
Kim, J. et al., Golden carbon nanotubes as multimodal photoacoustic and photothermal high-contrast molecular agents, Nature Nanotechnology, 4:688-694 (2009).
Kim, J. et al., Multifunctional nanostructured materials for multimodal imaging, and simultaneous imaging and therapy, Chem. Soc. Rev., 38:372-390 (2009).
Kircher, M.F. et al., A brain tumor molecular imaging strategy using a new triple-modality MRI-photoacoustic-Raman nanoparticle, Nature Medicine, 18(5):829-834 (2012).
Kircher, M.F. et al., Noninvasive cell-tracking methods, Nature Reviews: Clinical Oncology, 8:677-688 (2011).
Knauth, M. et al., Low-field interventional MRI in neurosurgery: finding the right dose of contrast medium, Neuroradiology, 43:254-258 (2001).
Knauth, M. et al., Surgically Induced Intracranial Contrast Enhancement: Potential Source of Diagnostic Error in Intraoperative MR Imaging, AJNR Am J Neuroradiol, 20:1547-1553 (1999).
Koljenovic, S. et al., Raman Spectroscopic Characterization of Porcine Brain Tissue Using a Single Fiber-Optic Probe, Anal. Chem., 79:557-564 (2007).
Loening, A.M. And Gambhir, S.S., Amide: A Free Software Tool for Multimodality Medical Image Analysis, Molecular Imaging, 2(3):131-137 (2003).
Lüdemann, L. et al., Pharmacokinetic analysis of glioma compartments with dynamic Gd-DTPA-enhanced magnetic resonance imaging, Magnetic Resonance Imaging, 18:1201-1214 (2000).
Maeda, H. et al., Tumor vascular permeability and the EPR effect in macromolecular therapeutics: a review, Journal of Controlled Release, 65:271-284 (2000).
Mansfield, J.R. et al., Autofluorescence removal, multiplexing, and automated analysis methods for in-vivo fluorescence imaging, Journal of Biomedical Optics, 10(4):041207-1-9 (2005).

McNay, G. et al., Surface-Enhanced Raman Scattering (SERS) and Surface-Enhanced Resonance Raman Scattering (SERRS): A Review of Applications, Applied Spectroscopy,565(8):825-837 (2011).
Ozawa, T. et al., Bromophenol Blue Staining of Tumors in a Rat Glioma Model, Neurosurgery, 57(4):1041-1047 (2005).
Pelletier, M.J., Quantitative Analysis Using Raman Spectrometry, 57(1):20A-42A (2003).
Razansky, D. et al., Multispectral opto-acoustic tomography of deep-seated fluorescent proteins in vivo, Nature Photonics, 3:412-417 (2009).
Reinges, M.H.T. et al., Course of brain shift during microsurgical resection of supratentorial cerebral lesions: limits of conventional neuronavigation, Acta Neurochir, 146:369-377 (2004).
Robbins, S.L. and Angell, M., Neoplasia and Other Disturbances of Cell Growth, Basic Pathology: Non-Neoplastic Cell Growth, 2(3):68-105 (1976).
Schneider, J.P. et al., Intraoperative MRI to guide the resection of primary supratentorial glioblastoma multiforme—a quantitative radiological analysis, Neuroradiology, 47:489-500 (2005).
Shinoda, J. et al., Fluorescence-guided resection of glioblastoma multiforme by using high-dose fluorescein sodium, J Neurosurg, 99:597-603 (2003).
Short, M.A. et al., Development and preliminary results of an endoscopic Raman probe for potential in vivo diagnosis of lung cancers, Optics Letters, 33(7):711-713 (2008).
Stewart et al., Raman Imaging, Annual Review of Analytical Chemistry, 5:337-360 (2012).
Stummer, W. et al., Fluorescence-guided surgery with 5-aminolevulinic acid for resection of malignant glioma: a randomised controlled multicentre phase III trial, Oncology: The Lancet, 7:392-401 (2006).
Stupp, R. et al., Changing Paradigms—An Update on the Multidisciplinary Management of Malignant Glioma, The Oncologist, 11:165-180 (2006).
Thakor, A.S. et al., Oxidative Stress Mediates the Effects of Raman-Active Gold Nanoparticles in Human Cells, Nanoparticle Cytotoxicity, 7(1):126-136 (2011).
Thakor, A.S. et al., The Fate and Toxicity of Raman-Active Silica-Gold Nanoparticles in Mice, Drug Delivery, Science Translation Medicine, 3(79):1-11 (2011).
Toms, S.A. et al., Intraoperative Optical Spectroscopy Identifies Infiltrating Glioma Margins with High Sensitivity, Operative Neurosurgery, 57(4):382-391 (2005).
Tréhin, R. et al., Fluorescent Nanoparticle Uptake for Brain Tumor Visualization, Neoplasia, 8(4):302-311 (2006).
Tuerk, C. and MacDougal-Waugh, S., In vitro evolution of functional nucleic acids: high-affinity RNA ligands of HIV-1 proteins, Gene, 137:33-39 (1993).
Wang, L.V., Multiscale photoacoustic microscopy and computed tomography, Nature Photonics, 3:503-209 (2009).
Written Opinion, PCT/US2013/057636, dated Jan. 3, 2014, 12 pages.
Written Opinion, PCT/US2013/076475, dated Jun. 16, 2014, 8 pages.
Written Opinion, PCT/US2014/017508 dated May 12, 2014, 12 pages.
Yigit, M.V. and Medarova, Z., In vivo and ex vivo applications of gold nanoparticles for biomedical SERS imaging, Am J Nucl Med Mol Imaging, 2(2):232-341 (2012).
Zavaleta, C. et al., Noninvasive Raman Spectroscopy in Living Mice for Evaluation of Tumor Targeting with Carbon Nanotubes, Nano Letters, 8(9):2800-2805 (2008).
Zavaleta, C.L. et al., Multiplexed imaging of surface enhanced Raman scattering nanotags in living mice using noninvasive Raman spectroscopy, PNAS, 106(32):13511-13516 (2009).
Zavaleta, C.L. et al., Preclinical Evaluation of Raman Nanoparticle Biodistribution for their Potential Use in Clinical Endoscopy Imaging, Small, 7(15):2232-2240 (2011).
Zavaleta, C.L. et al., Raman's "Effect" on Molecular Imaging, J Nucl Med., 52:1839-1844 (2011).
Zhang, Y. et al., Molecular Imaging with SERS-Active Nanoparticles, Small, 7(23):3261-3269 (2011).
Extended European Search Report for EP 13832980.0, 9 pages (dated Apr. 20, 2016).

(56) References Cited

OTHER PUBLICATIONS

Fales, A.M. et al., Silica-coated gold nanostars for combined surface-enhanced Raman scattering (SERS) detection and singlet-oxygen generation: a potential nanoplatform for theranostics, Langmuir, 27(19):12186-90 (2011).

Wieboldt, Dick, Understanding Raman Spectrometer Parameters, Spectroscopy, Special Issue, 6 pages (2010).

Debbage, P. and Jaschke, W., Molecular imaging with nanoparticles: giant roles for dwarf actors, Histochem. Cell Biol., 130(5):845-75 (2008).

Declaration of Moritz Kircher for U.S. Appl. No. 14/464,642, 16 pages, executed Dec. 5, 2016.

Huang, J. et al., Preparation of Silica-Encapsulated Hollow Gold Nanosphere Tags Using Layer-by-Layer Method for Multiplex Surface-Enhanced Raman Scattering Detection, Langmuir, 27:10228-10233 (2011).

Huang, R. et al., High Precision Imaging of Microscopic Spread of Blioblastoma with a Targeted Ultrasensitive SERRS Molecular Imaging Probe, Theranostics, 6(8):1075-1084 (2016).

Huang, X. et al., Gold nanoparticles: interesting optical properties and recent applications in cancer diagnostics and therapy, Nanomedicine, 2(5):681-693 (2007).

Kaaki, K. et al., Magnetic Nanocarriers of Doxorubicin Coated with Poly(ethylene glycol) and Folic Acid: Relation between Coating Structure, Surface Properties, Colloidal Stability, and Cancer Cell Targeting, Langmuir, 28:1496-1505 (2012).

Kim, K. et al., Silver-Coated Dye-Embedded Silica Beads: A Core Material of Dual Tagging Sensors Based on Fluorescence and Raman Scattering, ACS Applied Materials & Interfaces, 3:324-330 (2011).

Kim, K. et al., Silver-particle-based surface-enhanced resonance Raman scattering spectroscopy for biomolecular sensing and recognition, Anal Bioanal Chem., 388:81-88 (2007).

Kodali, A., et al., Optimally designed nanolayered metal-dielectric particles as probes for massively multiplexed and ultrasensitive molecular assays, PNAS, 107(31):13620-13625 (2010).

Lusic, H. and Grinstaff, M.W., X-ray-computed tomography contrast agents, Chem. Rev., 113(3):1641-66 (2013).

Massoud, T.F. and Gambhir, S.S., Molecular imaging in living subjects: seeing fundamental biological processes in a new light, Genes Dev., 17(5):545-80 (2003).

Qian, X. et al., In vivo tumor targeting and spectroscopic detection with surface-enhanced Raman nanoparticle tags, Nature Biotechnology, 26(1):83-90, (2008).

Stewart, S. et al., Raman Imaging, Annu. Rev. Anal. Chem. 5:337-360 (2012).

Supplementary Partial European Search Report, European International Application No. 14753802.9, 8 pages, dated Oct. 20, 2016.

Tognalli, N. et al., From Single to Multiple Ag-Layer Modification of Au Nanocavity Substrates: A Tunable Probe of the Chemical Surface-Enhanced Raman Scattering Mechanism, ACS Nano, 5(7):5433-5443 (2011).

Cheng, F. et al, Chelator-Free Synthesis of a Dual-Modality PET/MRI Agent, Angew. Chem. Int. Ed., 52: 13319-13323 (2013).

Harmsen, S. et al., Rational design of a chalcogenopyrylium-based surface-enhanced resonance Raman scattering nanoprobe with attomolar sensitivity, Nature Communications, 6:6570, pp. 1-9, Additional Information added, 8 pages (2015).

Lee, S. B. et al, Mesoporous Silica Nanoparticle Pretargeting for PET Imaging Based on a Rapid Bioorthogonal Reaction in a Living Body, Angew. Chem. Int. Ed., 52: 10549-10552 (2013).

Sun, X. et al, Self-Illuminating $^{64}$Cu-Doped CdSe/ZnS Nanocrystals in Vivo Tumor Imaging, Journal of the American Chemical Society, 136: 1706-1709 (2014).

Sá, L. T. M. et al, Development of Nanoptamers Using a Mesoporous Silica Model Labeled with $^{99m}$Tc for Cancer Targeting, Oncology, 82: 213-217 (2012).

Esenturk, E. N. and Walker, A. R. H., Surface-enhanced Raman scattering spectroscopy via gold nanostars, Journal of Raman Spectroscopy, 40(1): 86-91 (2009).

International Search Report for PCT/US2015/042441, 3 pages (dated Oct. 19, 2015).

Written Opinion for PCT/US2015/042441, 16 pages (dated Oct. 19, 2015).

Yi, Z. et al, Facile preparation of Au/Ag bimetallic hollow nanospheres and its application in surface-enhanced Raman scattering, Applied Surface Science, 258(1): 212-217 (2011).

Yigit, M. V. et al, Noninvasive MRI-SERS Imaging in Living Mice Using an Innately Bimodal Nanomaterial, ACS NANO, 5(2): 1056-1066 (2011).

Yuan, H. et al., Quantitative Surface-Enhanced Resonant Raman Scattering Multiplexing of Biocompatible Gold Nanostars for in Vitro and ex Vivo Detection, Analytical Chemistry, 85:208-212 (2012).

Zong, S. et al., A SERS and fluorescence dual mode cancer cell targeting probe based on silica coated Au@Ag core-shell nanorods, Talanta, 97:368-375 (2012).

Von Maltzahn, G. et al., SERS-Coded Gold Nanorods as a Multifunctional Platform for Densely Multiplexed Near-Infrared Imaging and Photothermal Heating, Adv. Mater. 21:3175-3180 (2009).

* cited by examiner

MULTIMODAL PARTICLES, METHODS AND USES THEREOF

CROSS-REFERENCE TO RELATED APPLICATIONS

This application is a 35 U.S.C. 371 National Stage of International Patent Application No. PCT/US2013/076475, filed Dec. 19, 2013, which designated the U.S. and which claims priority to and the benefit of, U.S. Provisional Patent Application No. 61/739,556, filed Dec. 19, 2012, the contents of each of which are entirely incorporated herein by reference.

GOVERNMENT SUPPORT

This invention was made with government support under NIH/NCI K08 CA163961 awarded by the National Institute of Health. The United States Government has certain rights in this invention.

BACKGROUND

Nanoparticle systems that can incorporate dopant entities have tremendous potential and are useful in a wide variety of contexts. There is a continuing need for improved nanoparticle systems, for both medical and/or non-medical applications. One particular goal in developing such systems is to provide imaging nanoparticles that can be utilized in surgery to define resection boundaries. Completeness of surgical resection profoundly impacts morbidity and mortality. The challenges and significance of complete resection are particularly acute in surgery to remove tumors. In trying to achieve more complete tumor resections, the surgeon encounters several hurdles, which include irregular and indistinct tumor margins as well as tumor growth adjacent to or invading crucial physiological structures. A wide variety of techniques have been explored to date in an effort to better visualize tumor margins. However, there remains a continuing need for new and better probes and/or methods. In particular, there is an important, unmet need for a real-time probe/method for accurately detecting residual tumor.

SUMMARY

The present invention encompasses the recognition that there is an important and unmet need for multimodal particles susceptible to imaging with a plurality of imaging modalities. The present invention further encompasses the recognition of a source of a problem with existing imaging technologies: current contrast agents are typically rapidly cleared so that each new imaging session requires a new injection. The present invention recognizes a variety of drawbacks associated with this reality, including that intraoperative imaging is often not practical, and sometimes not possible. The present invention provides technologies that can be imaged using any of a variety of modalities. In some embodiments, the invention provides contrast enhancement across a plurality of modalities and/or at a plurality of times (e.g., at preoperative, intra-operative, and post-operative stages) with a delivery event (e.g., a single injection such as an intravenous injection).

The present invention provides technologies relevant to multilayered particles, including technologies for preparing particles, and/or for using particles, as well as providing particles themselves. In general, particles as described and/or utilized herein contain a substrate, and a plurality of layers, wherein at least one layer contains a dopant entity. In some embodiments, at least two layers contain dopant entities. In some such embodiments, provided particles contain at least two different dopant entities, optionally localized in different layers. In some embodiments, a single entity (e.g., a particular doping entity, substrate, or layer material) is itself useful by two or more modalities (e.g., diagnostic and/or therapeutic modalities).

In some embodiments, provided particles are susceptible to detection by two or more detection modalities. In some embodiments, one or more of the substrate, a layer material, and/or a dopant entity is detectable. In some embodiments, the detectable entity(ies) act as contrast agents. In some embodiments, a single entity (e.g., a particular doping entity, substrate, or layer material) is itself detectable by two or more modalities.

In some embodiments, one remarkable feature of provided technologies is that they are applicable to and effective with a wide range of substrate materials, substrate configurations, layer materials and dopant entities, etc. Furthermore, the ability to provide individual particles that can be successfully imaged by a plurality of different imaging modalities is unique to the present invention. In some such embodiments, each imaging modality has its own strength. Such embodiments have unique advantages in that ability to detect the particles with different imaging technologies that are complementary to one another can permit visualization of particles in any of a variety of settings such as, for example, presurgical (e.g., noninvasive whole body 3D imaging for initial tumor detection, whole body staging, and surgical planning), intraoperative, or endoscopic (e.g., imaging by insertion of thin catheters, fiberoptic devices, laparoscopic instruments, etc. into the body) scenario.

Some embodiments of the present invention therefore provide, among other things, systems for imaging the same particle with multiple imaging modalities and/or in multiple settings. Alternatively or additionally, some embodiments of the present invention provide methods that include a single administration of particles to a subject, followed by a plurality of steps that include imaging the administered particles, which steps may utilize different imaging technologies and/or be performed at different times and/or in different environments.

In some embodiments, provided particles comprise first and second dopant entities in first and second layers, respectively. In certain embodiments, the first dopant entity is or comprises a SE(R)RS-active agent and the second dopant entity is or comprises another detectable entity selected from the group consisting of SE(R)RS-active agent, fluorochromes, MRI agents, photoacoustic-active dyes, upconverting materials, positron emission tomography (PET) tracers, single photon emission tomography (SPECT) tracers, computed tomography (CT) agents, X-Rays agents, ultrasound (US) agents and combinations thereof. In some embodiments, such particles are particularly useful for in vivo imaging applications.

In some embodiments, provided particles are imaged (or susceptible to imaging) by an imaging modality selected from the group consisting of MRI, PET, SPECT, CT, X-ray, ultrasound, photoacoustic detection, fluorescent and/or Raman spectroscopy, and combinations thereof.

In some embodiments, provided particles comprise one or more carrier or buffer layers. Without wishing to be bound to any particular theory, particles described in some embodiments provide remarkable advantages in separating dopant entities. Such separation can minimize or avoid interference or contamination of different imaging signals.

Some aspects of the present invention relate to a composition comprising at least one particle comprised of a substrate; at least a first layer comprising at least a first dopant entity; and at least a second layer comprising a second dopant entity.

Some aspects of the present invention relate to a composition comprising at least one particle comprised of a substrate; at least a first layer, which may be a condensation layer and/or an encapsulant layer, comprising at least a first dopant entity; and at least a second layer comprising a second dopant entity.

In some embodiments, some or all layers have a thickness within the range of about 0.5 nm to about 5 μm. In some embodiments, the dopant entity is positioned within 5 nm, 10 nm, 15 nm, 20 nm, 25 nm, 30 nm, 35 nm, 40 nm, 45 nm, 50 nm or 100 nm or 5 μm of the substrate's surface. In some embodiments, a condensation or an encapsulant layer is or comprises a material selected from the group consisting of metal, semi-metal, non-metal, oxides, borides, carbides, sulfides and nitrides of the metal, semi-metal or non-metal, and combinations thereof. In some embodiments, the metal, semi-metal or non-metal is or comprises silica, titania, zirconia, germania, alumina, tantalum pentoxide, or combinations thereof. In some embodiments a condensation layer or an encapsulant layer compromises polypeptides, oligomers, or polymers, that embed, coordinate to, or are covalently bound to contrast agents from the group of MRI, PET, SPECT, CT, X-ray, ultrasound, photoacoustic detection, fluorescent and/or Raman spectroscopy, and combinations thereof.

In some embodiments, the second layer is a second condensation layer or a second encapsulant layer. In some embodiments, some or all layers are comprised of the same material(s). In some embodiments, some or all layers are silica layers. In some embodiments, at least first and second layers comprise first and second dopant entities, respectively. In some embodiments, the first and second dopant entities are the same. In some embodiments, the first and second dopant entities are different. In some embodiments, at least one of the first and second dopant entities is or comprises a detectable entity. In some embodiments, the detectable entity is selected from the group consisting of SE(R)RS-active agent, fluorochromes, MRI agents, photoacoustic-active dyes, upconverting materials, positron emission tomography (PET) tracers, single photon emission tomography (SPECT) tracers, computed tomography (CT) agents, X-Ray agents, ultrasound (US) agents, and combinations thereof. In some embodiments, at least one of the first and second dopant entities is or comprises a SE(R)RS-active agent. In some embodiments, the first dopant entity is or comprises a SE(R)RS-active agent and the second dopant entity is or comprises a second detectable entity. In some embodiments, the second detectable entity is a NIR fluorescent agent.

In some embodiments, the composition further includes a third detectable entity. In some embodiments, at least one of the first and second dopant entities is an agent other than a detectable entity so that the layer comprising the agent is a carrier layer. In some embodiments, the composition further includes a buffer layer that lacks a dopant entity. In some embodiments, the buffer layer is positioned between the first and second layers.

In some embodiments, the dopant entities are directly associated within the layers. In some embodiments, the dopant entities are indirectly associated within the layers via a linker, or a chelator.

In some embodiments, the substrate is spherical. In some embodiments, the substrate is non-spherical. In some embodiments, the substrate is or comprises a material selected from the group consisting of metals, metal oxides, liposomes, upconverting materials, semiconductors, and combinations thereof. In some embodiments, the metal is selected from the group consisting of gold, silver, copper, or any other material capable of sustaining localized surface plasmon resonance, and combinations thereof. In some embodiments, the substrate is associated with surface primers.

In some embodiments, the substrate is associated with capping agent entities. In some embodiments, the particle is substantially free of surface primers. In some embodiments, the composition has a diameter within the range of about 5 nm to about 1000 nm or about 5 nm to about 200 nm.

One aspect of the present invention relates to a method of preparing a particle. The method includes providing a first precursor solution of a layer (e.g., which may be a condensation layer and/or an encapsulant layer) in water and alcohol, wherein the first precursor solution has a predetermined water content; combining the first precursor solution with a substrate under conditions and for a time necessary and sufficient to apply onto the substrate the first layer, which first layer has a predetermined thickness, resulting in a particle.

In some embodiments, the substrate further includes at least one layer. In some embodiments, the steps of providing and combining are performed at the same time so that the first precursor solution and the substrate are mixed with one another simultaneously.

In some embodiments, the method further includes combining a first dopant entity with the first precursor solution. In some embodiments, the method further includes providing a second precursor solution for a second layer (e.g., which may be a condensation layer and/or an encapsulant layer) in water and alcohol. In some embodiments, the method further includes combining the second precursor solution with the particle under conditions and for a time necessary and sufficient to apply onto the particle the second layer, which second layer has a second predetermined thickness. In some embodiments, the method further includes combining a second dopant entity with the second precursor solution.

One aspect of the present invention relates to a method including a step of providing to a site of interest a collection of particles each comprised of a substrate; at least a first layer, which may be a condensation layer and/or an encapsulation layer, comprising at least a first dopant entity; and at least a second layer comprising a second dopant entity.

In some embodiments, the site of interest is or comprises a solid tumor. In some embodiments, the solid tumor is selected from the group consisting of brain, lung, breast, ovary, stomach, pancreas, larynx, esophagus, testes, liver, parotid, biliary tract, colon, rectum, cervix, uterus, endometrium, kidney, bladder, prostate, thyroid, head and neck, melanomas, gliomas, neuroblastomas, and neuroendocrine tumors. In some embodiments, the step of providing includes administering the collection of particles to a location and in an amount such that particles from the collection localize to the solid tumor.

In some embodiments, the particles further comprise a targeting entity. In some embodiments, the substrate is gold. In some embodiments, the first dopant entity is a SE(R)RS-active agent or a photoacoustic dye. In some embodiments, the second dopant entity is a NIR fluorescent agent.

In some embodiments, the particles further comprise MRI agents, photoacoustic-active dyes, upconverting materials, positron emission tomography (PET) tracers, single photon emission tomography (SPECT) tracers, computed tomography (CT) agents, X-Rays agents, ultrasound (US) agents and combinations thereof. In some embodiments, each of the first and second dopant entities include an entity selected from the group consisting of radionuclides, fluorescent dyes, and combinations thereof.

In some embodiments, the method further includes a step of imaging administered particles. In some embodiments, the method further includes a plurality of steps of imaging administered particles. In some embodiments, different imaging modalities are utilized in different imaging steps. In some embodiments, different imaging steps utilizing different imaging modalities are performed substantially simultaneously.

In some embodiments, different imaging steps utilizing different imaging modalities are performed at different times or in different environments. In some embodiments, wherein each imaging step of the plurality of imaging steps comprises utilizing an imaging modality selected from the group consisting of MRI, PET, SPECT, CT, X-ray, ultrasound, photoacoustic detection, fluorescent/Raman spectroscopy, and combinations thereof.

In some embodiments, the method further includes a first step of imaging administered particles, wherein the radionuclide generates Cerenkov signal. In some embodiments, the method further includes a second step of imaging administered particles, wherein the radionuclide causes secondary Cerenkov induced fluorescence.

Definitions

In order for the present disclosure to be more readily understood, certain terms are defined below. Additional definitions for, or clarifications of, the following terms and other terms may be set forth throughout the specification.

In this application, the use of "or" means "and/or" unless stated otherwise. As used in this application, the term "comprise" and variations of the term, such as "comprising" and "comprises," are used in situations where listed items, elements, or steps are included and others may also be included. As used in this application, the terms "about" and "approximately" are used as equivalents. Any numerals used in this application, whether or not preceded by "about" or "approximately" are meant unless otherwise indicated to cover any normal fluctuations (e.g., standard errors or deviations), as would be appreciated by one of ordinary skill in the relevant art. In certain embodiments, the terms "approximately" or "about" refer to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Administration": The term "administration" refers to introducing a substance into a subject. In general, any route of administration may be utilized including, for example, by inhalation (e.g., nasal), by introduction into the cerebrospinal fluid, or by introduction into a body cavity, compartment, or tissue. In some embodiments, administration is parenteral (e.g., intra-arterial, intravenous, peritoneal, subcutaneous), oral, topical, rectal, vaginal, etc. In some embodiments, administration is oral. Additionally or alternatively, in some embodiments, administration is parenteral. In some embodiments, administration is intravenous. In some embodiments, administration is systemic; in some embodiments, administration is local. In some embodiments, administration is into a body cavity, compartment, or tissue, for example during surgery.

"Associated": As used herein, the term "associated" typically refers to two or more entities in physical proximity with one another, either directly or indirectly (e.g., via one or more additional entities that serve as a linking agent), to form a structure that is sufficiently stable so that the entities remain in physical proximity under relevant conditions, e.g., physiological conditions. In some embodiments, associated moieties are covalently linked to one another. In some embodiments, associated entities are non-covalently linked. In some embodiments, associated entities are linked to one another by specific non-covalent interactions (i.e., by interactions between interacting ligands that discriminate between their interaction partner and other entities present in the context of use, such as, for example. streptavidin/avidin interactions, antibody/antigen interactions, etc.). Alternatively or additionally, a sufficient number of weaker non-covalent interactions can provide sufficient stability for moieties to remain associated. Exemplary non-covalent interactions include, but are not limited to, affinity interactions, metal coordination, physical adsorption, host-guest interactions, hydrophobic interactions, pi stacking interactions, hydrogen bonding interactions, van der Waals interactions, magnetic interactions, electrostatic interactions, dipole-dipole interactions, etc.

"Biocompatible": The term "biocompatible", as used herein is intended to describe materials that do not elicit a substantial detrimental response in vivo. In certain embodiments, the materials are "biocompatible" if they are not toxic to cells. In certain embodiments, materials are "biocompatible" if their addition to cells in vitro results in less than or equal to 20% cell death, and/or their administration in vivo does not induce inflammation or other such adverse effects. In certain embodiments, materials are biodegradable.

"Biodegradable": As used herein, "biodegradable" materials are those that, when introduced into cells, are broken down by cellular machinery (e.g., enzymatic degradation) or by hydrolysis into components that cells can either reuse or dispose of without significant toxic effects on the cells. In certain embodiments, components generated by breakdown of a biodegradable material do not induce inflammation and/or other adverse effects in vivo. In some embodiments, biodegradable materials are enzymatically broken down. Alternatively or additionally, in some embodiments, biodegradable materials are broken down by hydrolysis. In some embodiments, biodegradable polymeric materials break down into their component polymers. In some embodiments, breakdown of biodegradable materials (including, for example, biodegradable polymeric materials) includes hydrolysis of ester bonds. In some embodiments, breakdown of materials (including, for example, biodegradable polymeric materials) includes cleavage of urethane linkages.

"Condensation layer": The term "condensation layer" refers to a layer assembled from a plurality of precursor units. In some embodiments, such assembly involves a traditional condensation reaction (e.g., resulting in release of water); however, those of ordinary skill in the art reading the present specification will appreciate that the term "condensation layer" is not limited to layers formed by any particular chemistry. Any layer that satisfies the requirements and description herein is a "condensation layer".

"Dopant Entity": The term "dopant entity" refers to any material, molecule, or atom, that is not intrinsically part of the condensation or the encapsulant layer. It refers to any material, molecule, imaging agent, therapeutic agent, that is embedded in, coordinated to, or (covalently) associated with the condensation or the encapsulant layer.

"Encapsulant layer": The term "encapsulant layer" refers to a layer that encapsulates a surface (e.g., of a substrate or another layer) to which it is applied and/or a dopant entity. In some embodiments, an encapsulant layer substantially covers the surface or dopant entity. In some embodiments, an encapsulant layer is a condensation layer in that it is assembled from a plurality of precursor units. In some embodiments, such assembly involves a traditional condensation reaction (e.g., resulting in release of water); however, those of ordinary skill in the art reading the present specification will appreciate that the term "encapsulant layer" is not limited to layers formed by any particular chemistry. Those skilled in the art, reading the present specification in context, will well understand the metes and bounds of what may be an "encapsulant layer" in accordance with the present invention.

"Illuminating": The term "illuminating" as used herein refers to application of a light source such as, for example, a near-infrared (NIR), visible, or ultraviolet (UV) light source. In some embodiments, illuminating comprises applying laser light. In some embodiments, illuminating comprises applying light of a wavelength appropriate to excite one or more responsive agents; in some such embodiments, responsive agents are comprised in provided particles. For example, one or more dopant entities, layers, and/or substrates may be or comprise a light-responsive agent.

"Magnetic Resonance Imaging": The term "magnetic resonance imaging (MRI)" as used herein refers to a medical imaging technique most commonly used in radiology to visualize the structure and function of the body. It provides detailed images of the body in any plane. MRI uses no ionizing radiation, but uses a powerful magnetic field to align the nuclear magnetization of (usually) hydrogen atoms in water in the body. Radiofrequency fields are used to systematically alter the alignment of this magnetization, causing the hydrogen nuclei to produce a rotating magnetic field detectable by the scanner. This signal can be manipulated by additional magnetic fields to build up enough information to construct an image of the body. When a subject lies in a scanner, the hydrogen nuclei (i.e., protons) found in abundance in an animal body in water molecules, align with the strong main magnetic field. A second electromagnetic field that oscillates at radiofrequencies and is perpendicular to the main field, is then pulsed to push a proportion of the protons out of alignment with the main field. These protons then drift back into alignment with the main field, emitting a detectable radiofrequency signal as they do so. Since protons in different tissues of the body (e.g., fat versus muscle) realign at different speeds, the different structures of the body can be revealed. Contrast agents may be injected intravenously to enhance the appearance of blood vessels, tumors or inflammation. MRI is used to image every part of the body, but is particularly useful in neurological conditions, disorders of the muscles and joints, for evaluating tumors and showing abnormalities in the heart and blood vessels.

"Sample": The term "sample" refers to a volume or mass obtained, provided, and/or subjected to analysis. In some embodiments, a sample is or comprises a tissue sample, cell sample, a fluid sample, and the like. In some embodiments, a sample is taken from a subject (e.g., a human or animal subject). In some embodiments, a tissue sample is or comprises brain, hair (including roots), buccal swabs, blood, saliva, semen, muscle, or from any internal organs, or cancer, precancerous, or tumor cells associated with any one of these. A fluid may be, but is not limited to, urine, blood, ascites, pleural fluid, spinal fluid, and the like. A body tissue can include, but is not limited to, brain, skin, muscle, endometrial, uterine, and cervical tissue or cancer, precancerous, or tumor cells associated with any one of these. In an embodiment, a body tissue is brain tissue or a brain tumor or cancer. Those of ordinary skill in the art will appreciate that, in some embodiments, a "sample" is a "primary sample" in that it is obtained from a source (e.g., a subject); in some embodiments, a "sample" is the result of processing of a primary sample, for example to remove certain potentially contaminating components and/or to isolate or purify certain components of interest.

"Substantially": As used herein, the term "substantially", and grammatical equivalents, refer to the qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result.

"Subject": As used herein, the term "subject" includes humans and mammals (e.g., mice, rats, pigs, cats, dogs, and horses). In many embodiments, subjects are be mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments, (e.g., particularly in research contexts) subject mammals will be, for example, rodents (e.g., mice, rats, hamsters), rabbits, primates, or swine such as inbred pigs and the like.

BRIEF DESCRIPTION OF THE DRAWING

The Drawing, which is comprised of at least the following Figures, is for illustration purposes only, not for limitation.

As shown in FIG. 4, the Raman signal outlines the tumor.

DETAILED DESCRIPTION OF CERTAIN EMBODIMENTS

Figure 1:
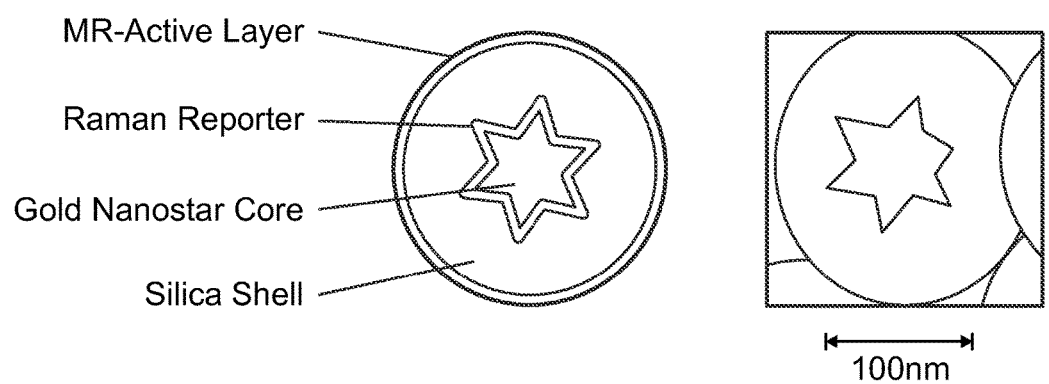
FIG. 1 shows a schematic of a SE(R)RS particle in accordance with the present invention together with a transmission electron micrograph (TEM) of a representative SE(R)RS particle. At the center of the SE(R)RS particle is a gold nanostar substrate coated with a layer of (resonance) Raman-active molecules (reporters). The star shape enables tuning of the Localized Surface Plasmon Resonance (LSPR) towards the Near-Infrared window and incorporates several "hot-spots" (the tips) of incredibly concentrated electric fields focused on the (resonance) Raman reporters. A shell of silica encapsulates this substrate, simultaneously protecting the (resonance) Raman reporters, preventing reactions of the substrate and reporters with the environment, and providing a surface for further functionalization. In this case, an MR-active layer is bound to the outer surface of the silica.

Embodiments of the present disclosure provides for particles, methods of making particles, methods of using particles and the like. For some embodiments, useful reference can be made, for example, to U.S. Provisional Patent Application No. 61/696,122, filed Aug. 31, 2012, entitled "PARTICLES, METHODS AND USES THEREOF", the contents of which are incorporated herein by reference, and/or to Examples 1-3.

Particles

Particles used in accordance with the present disclosure, in theory, can be of any shape (regular or irregular) or design. In some embodiments, a particle can be or comprise a sphere. Additionally or alternatively, a particle can be or comprises a star, a rod, a cube, a cuboid, a cone, a pyramid, a cylinder, a prism, a tube, a ring, a tetrahedron, a hexagon, an octagon, a cage, or any irregular shapes. In some embodiments, a particle has a shape corresponding to that of its substrate; in some embodiments, a particle has a shape different from that of its substrate. In some embodiments, where the particle and substrate have different shapes, one or more layers applied to the substrate has a thickness that varies at different locations within the particle.

In some embodiments, the greatest dimension or at least one dimension of a particle may be about or less than 10 μm, 5 μm, 1 μm, 800 nm, 500 nm, 400 nm, 300 nm, 200 nm, 180 nm, 150 nm, 120 nm, 110 nm, 100 nm, 90 nm, 80 nm, 70 nm, 60 nm, 50 nm, 40 nm, 30 nm, 20 nm, 10 nm, 5 nm, 2 nm, or even 1 nm. In some embodiments, the greatest dimension or at least one dimension of a particle may be more than 10 μm, 5 μm, 1 μm, 800 nm, 500 nm, 400 nm, 300 nm, 200 nm, 180 nm, 150 nm, 120 nm, 110 nm, 100 nm, 90 nm, 80 nm, 70 nm, 60 nm, 50 nm, 40 nm, 30 nm, 20 nm, 10 nm, 5 nm, 2 nm, or even 1 nm. In some embodiments, the greatest dimension or at least one dimension of a particle may be in a range of about 1 μm to about 5 nm or about 200 nm to about 5 nm. In some embodiments, the greatest dimension or at least one dimension of a particle may be in a range of about 300 nm to about 50 nm. In some embodiments, the greatest dimension or at least one dimension of a particle may be in a range of about 130 nm to about 90 nm. In some embodiments, the greatest dimension or at least one dimension of a particle may be in a range of any two values above. In some embodiments, the dimension of a particle is a diameter, wherein the diameter can be in a range as mentioned above. In some embodiments, the dimensions of a particle can be represented by a length, a width or a height in X, Y and Z-axis, wherein each dimension can be in a range as mentioned above.

It will be appreciated by those skilled in the art that particular sizes and/or shapes may be especially desirable or useful in different contexts. For example, particles for in vivo application typically have a size range from about 0.5 nm to about 200 nm; particles for in vitro application can have a size range from about 10 nm to about 1000 nm.

In some embodiments, particle sizes and surface charges are tuned to be provided to sites of interest for certain applications. In many embodiments, a site of interest is a tumor. In some embodiments, particles are designed and constructed to enter tumors via their leaky vasculature. In some embodiments, particles are designed and constructed to enter and/or be retained in tumors via phagocytosis by tumor (associated) cells (known as "enhanced permeability and retention (EPR)" effect). In certain embodiments, particles do not wash out of a tumor, but are retained stably within the tumor (e.g., retention time at least 7 days).

In various embodiments, a particle described herein can comprise a substrate, a plurality of layers (including one or more condensation and/or encapsulant layers; in some embodiments, at least two condensation and/or encapsulant layers), and one or more dopant entities (in some embodiments, at least two dopant entities). In some embodiments, particles are susceptible to imaging by multiple modalities. For example, FIG. 12 depicts an embodiment of a particle provided in accordance with the present invention.

Figure 12:
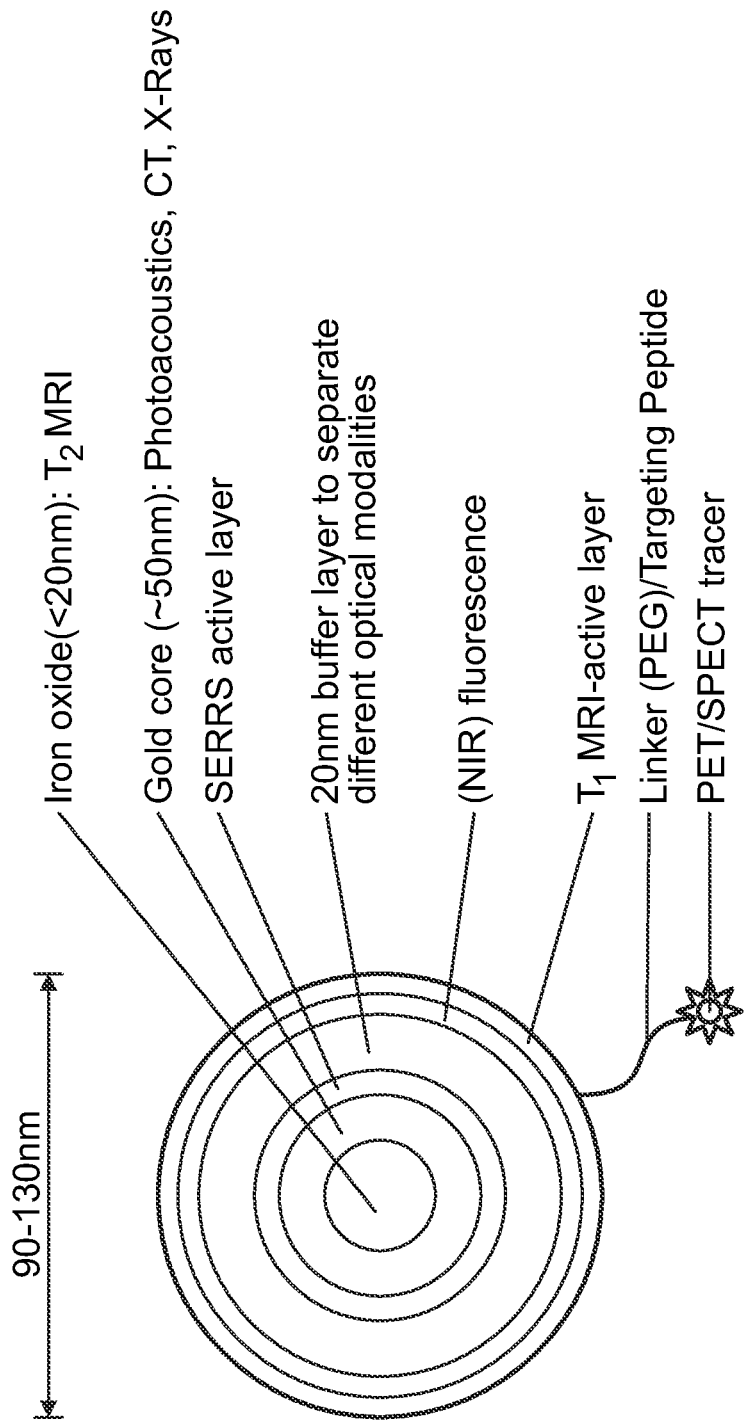
FIG. 12 shows a schematic of a multilayered particle in accordance with some embodiments of the present invention.

Referring to FIG. 12, in certain embodiments, a substrate comprises iron oxide for T2 MRI and/or gold substrate for photoacoustics, CT, and X-Rays. In certain embodiments, a plurality of layers are or comprise silica. In certain embodiments, the closest layer to a substrate comprises a surface-enhanced resonance Raman scattering (SE(R)RS)-active agent. In certain embodiments, such a particle further comprises an outer layer doped with a NIR fluorescent agent. In certain embodiments, there is a buffer layer between the two layers. In certain embodiments, provided particles can be employed with other agents such as MRI, PET, SPECT, CT, X-Rays or US agents.

Substrate

In accordance with some embodiments of the present invention, a particle has at least one substrate, which can be or comprise one or more materials, for example depending on applications for which the particle will be utilized. Exemplary substrate materials include, but are not limited to, metals, non-metals, and semi-metals, or oxides thereof (e.g., metal oxides, non-metal oxides, or semi-metal oxides) (e.g., iron oxide as illustrated in FIG. 12), liposomes, upconverting materials, semiconductors, and combinations thereof. Any materials used in a layer described below can be used as materials of a substrate. In some embodiments, a layer can be a particle's substrate. In some embodiments, photoacoustic and/or photothermal enhancements can be achieved by associating agents/molecules which induce surface phonon/plasmon enhancement, within the substrate or layers.

In some embodiments, a substrate can be or contain any metal or any other material capable of generating localized surface plasmon resonances (LSPRs). In many embodiments, a metal is a SE(R)RS active metal. Such a metal can be any (metallic) substance capable of sustaining a (localized) surface plasmon resonance. In some embodiments, a SE(R)RS active metal is or comprises Au, Ag, Cu, Na, K, Cr, Al, or Li. In some embodiments, a SE(R)RS active metal is an element selected from the group comprising Au, Ag, Cu, Na, K, Cr, Al, or Li. In some embodiments, a substrate can also contain alloys of metals. In some embodiments, a substrate is or contains Au, Ag or a combination thereof. In certain embodiments, a substrate can provide a detectable photoacoustic signal.

A substrate can be of any shape or design, and may contain one or more structural elements. In some embodiments, a nanoscale or at least one structural element of it is spherical. In some embodiments, a substrate or at least one structural element of it is non-spherical. In some embodiments, a substrate has structural elements selected from the group consisting of spheres, rods, stars, shells, ellipses, triangles, cubes, cages, pyramids and combinations thereof. For example, in some embodiments, a substrate can consist of or comprise a star overlaid with at least one shell. In some embodiments, a substrate can consist of or comprise two or more concentric shells. In some embodiments, a substrate can consist of or comprise a central structure surrounded by satellite structures.

In some embodiments, the greatest dimension or at least one dimension of a substrate or its each component may be about or less than 5 μm, 1 μm, 800 nm, 500 nm, 400 nm, 300 nm, 200 nm, 100 nm, 90 nm, 80 nm, 70 nm, 60 nm, 50 nm, 40 nm, 30 nm, 20 nm, 15 nm, 10 nm, 5 nm, 2 nm, 1 nm or 0.5 nm. In some embodiments, the greatest dimension or at least one dimension of a substrate or its each component may be more than 5 μm, 1 μm, 800 nm, 500 nm, 400 nm, 300 nm, 200 nm, 100 nm, 90 nm, 80 nm, 70 nm, 60 nm, 50 nm, 40 nm, 30 nm, 20 nm, 15 nm, 10 nm, 5 nm, 2 nm, 1 nm or 0.5 nm. In some embodiments, the greatest dimension or at least one dimension of a substrate or its each component may be in a range of about 500 nm to about 5 nm or about 150 nm to about 5 nm. In some embodiments, the greatest dimension or at least one dimension of a substrate or its each component may be in a range of about 100 nm to about 90 nm, about 90 nm to about 80 nm, about 80 nm to about 70 nm, about 70 nm to about 60 nm, about 60 nm to about 50 nm, about 50 nm to about 40 nm, about 40 nm to about 30 nm, about 30 nm to about 20 nm, about 20 nm to about 10 nm, about 10 nm to about 5 nm. In some embodiments, the greatest dimension or at least one dimension of a substrate or its each component may be in a range of any two values above.

A substrate with a desired size can be grown as metal colloids by a number of techniques well known in the art. For example, chemical or photochemical reduction of metal ions in solution using any number of reducing agents has been described. Likewise, syntheses of substrates can be carried out in constrained volumes, e.g., inside a vesicle. Substrates can also be made via electrical discharge in solution. Substrates can also be made by irradiating a metal with a high intensity pulsed laser.

Layers

Particles provided by the present invention may include a plurality of layers. In some embodiments, one or more inner layers can construct a particle's substrate.

In some embodiments, a layer substantially covers at least one surface of the substrate (or of another layer that itself substantially covers at least one surface of the substrate or of another layer). In some such embodiments, a layer substantially encapsulates the substrate.

In some embodiments, adjacent layers are in direct physical contact with one another; in some embodiments, adjacent layers are separated from one another so that an inter-layer space is defined between them; in some embodiments, such an inter-layer space is empty; in some embodiments, such an inter-layer contains liquid, etc.

A layer can have any size and shape. In some embodiments, a layer can be porous. In some embodiments, a layer is in a shape of a thin stripe or mat. In some embodiments, one or more layers substantially or partially cover the surface of a substrate or another layer.

Figure 13:
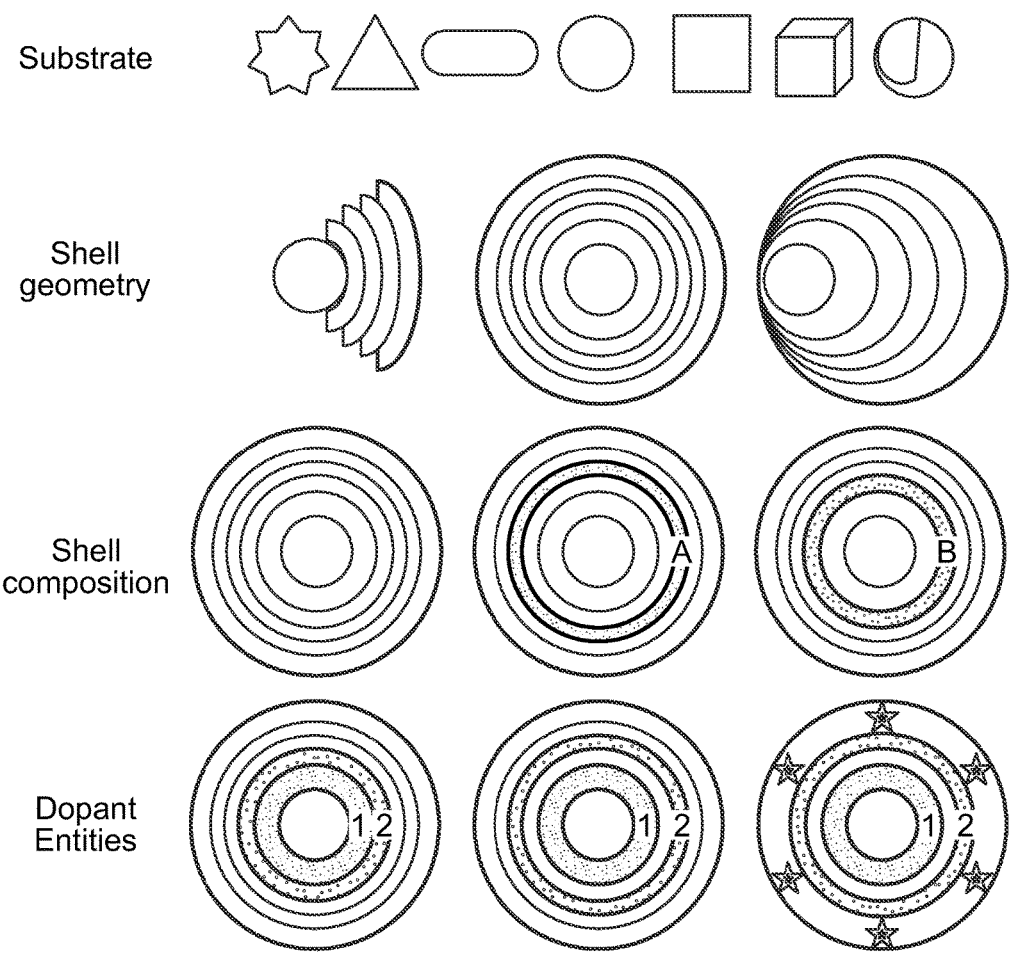
FIG. 13 illustrates exemplary substrates, shell geometry, shell composition and dopant entities for a particle described in some embodiments of the present invention.

In some embodiments, layers are arranged as shells. Referring to FIG. 13, at least two shells can be partially extended from at least one substrate, concentrically extended from at least one substrate, or extended asymmetrically from at least one substrate. Shells can have equal thicknesses, but can also have different thicknesses.

A plurality of layers each can respectively contain one or more materials. Layers (e.g., shells as illustrated in FIG. 13) can be or comprise, but are not limited to, one and the same material (e.g., including, but not limited to, compounds/materials from the group of metal/semi-metal/non-metal, -oxides, -sulfides, -carbides, -nitrides), layers can include at least two different materials (indicated by light grey color and dark grey/"A"; e.g., from the groups of metal/semi-metal/non-metal, -oxides, -sulfides, -carbides, -nitrides, polymers, and combinations thereof), layers can include the same or different materials in any combination (e.g., including, but not limited to, compounds/materials from the groups of metal/semi-metal/non-metal, -oxides, -sulfide, -carbides, -nitrides, ((bio-)degradable) polymers, (poly)peptides, nucleic acids (DNA), and combinations thereof) with at least one of them being porous (indicated by "B").

In some embodiments, a layer is synthesized by reacting precursors and the resulting layer is a condensation and/or an encapsulant layer. Particles described herein, in some embodiments, comprise at least one layer that is a condensation layer and/or an encapsulant layer, and at least another layer, where the at least another layer can also be a condensation and/or an encapsulant layer or any other layers.

According to various embodiments of the present disclosure, a layer can be or comprise metal (e.g., gold, silver, and the like), semi-metal or non-metal, and metal/semi-metal/non-metal oxides including silica ($SiO_2$), titania ($TiO_2$), alumina ($Al_2O_3$), zirconia ($ZrO_2$), germania ($GeO_2$), tantalum pentoxide ($Ta_2O_5$), $NbO_2$, etc., and non-oxides including metal/semi-metal/non-metal borides, carbides, sulfide and nitrides, such as titanium and its combinations (Ti, $TiB_2$, TiC, TiN, etc.).

Additionally or alternatively, materials of a layer can be polymers including PEG and PLGA/PEG, polypeptides, and polymeric chelators (e.g., poly DOTA, dendrimer backbone, poly DTPA, or dendrimer alone), (multiwalled) carbon nanotubes, graphene, silicone, peptides, nucleic acids, and any combinations thereof.

In some embodiments, each layer in a particle can be or contain the same material(s). For example, in some embodiments such as the ones described in the Examples below, the multilayers in the particles are silica layers.

In some embodiments, a layer is or includes silica. For example, a silica layer can be synthesized from a silica precursor including, but not limited to, alkylalkoxysilane; ethylpolysilicate; tetraethylorthosilicate (TEOS); tetramethylorthosilicate (TMOS); partially hydrolyzed TEOS; partially hydrolyzed TMOS, or any combination thereof.

In some embodiments, the present invention provides technologies that permit control of layer thickness. For example, in some embodiments, layer thickness is controlled by selection of solvent composition and/or content in the precursor solution. For example, in some embodiments, where a solvent composition comprising water is utilized, water content can control layer thickness. For example, in some embodiments, (see, e.g., Example 4 herein), the well-known Stöber method can be adapted for use in preparing one or more silica layers in accordance with the present disclosure. In some embodiments, the synthesis involves using a solution of one or more precursors in water and alcohol(s). A water content as used herein refers to the ratio of the volume of water to the total volume of a precursor solution.

Figure 14:
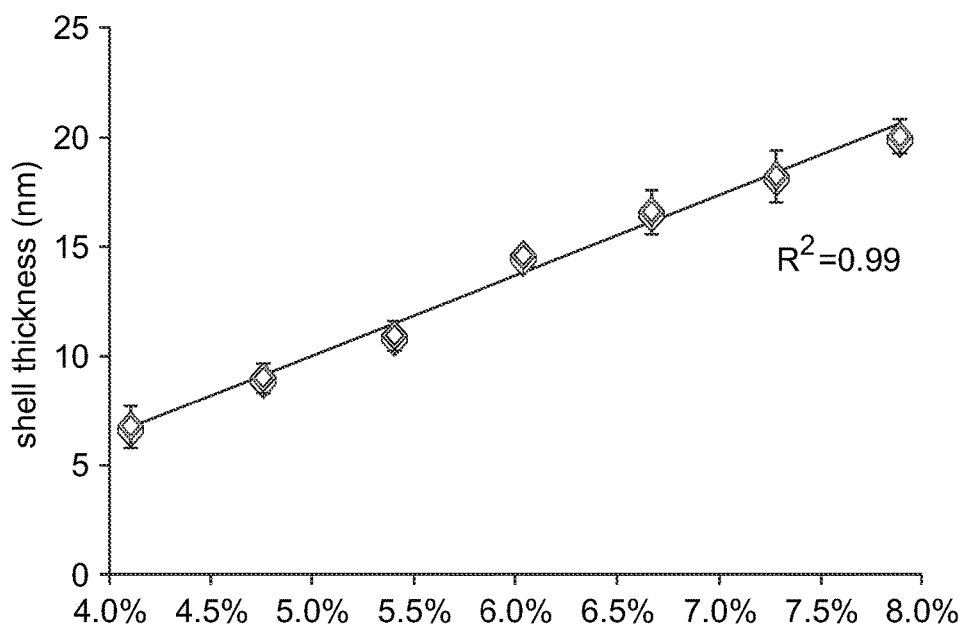
FIG. 14 is a plot of water contents versus shell thickness of exemplary particles, according to some embodiments of the present invention.

As illustrated in FIG. 14, in some embodiments, condensation reactions utilizing a water-containing solvent achieve different layer thicknesses with different water content. In some embodiments, a water content for synthesis is about 1.0 v/v/%, about 2.0 v/v %, about 3.0 v/v %, about 4.0 v/v %, about 4.5 v/v %, about 5.0 v/v %, about 5.5 v/v %, about 6.0 v/v %, about 6.5 v/v %, about 7.0 v/v %, about 7.5 v/v %, about 8.0 v/v %, about 8.5 v/v %, about 9.0 v/v %, about 9.5 v/v %, or about 10.0 v/v %. In some embodiments, water content for synthesis is in a range of any two values above.

In some embodiments, a layer is or includes one or more polymers, particularly polymers that which have been approved for use in humans by the U.S. Food and Drug Administration (FDA) under 21 C.F.R. § 177.2600, including, but not limited to, polyesters (e.g., polylactic acid, poly(lactic-co-glycolic acid), polycaprolactone, polyvalerolactone, poly(1,3-dioxan-2-one)); polyanhydrides (e.g., poly (sebacic anhydride)); polyethers (e.g., polyethylene glycol); polyurethanes; polymethacrylates; polyacrylates; polycyanoacrylates; copolymers of PEG and poly(ethylene oxide) (PEO).

In some embodiments, a layer is or includes at least one degradable material. Such a degradable material can be hydrolytically degradable, biodegradable, thermally degradable, enzymatically degradable, and/or photolytically degradable polyelectrolytes. In some embodiments, degradation may enable release of one or more dopant entities (e.g., agent for delivery) associated with a particle described herein.

Degradable polymers known in the art, include, for example, certain polyesters, polyanhydrides, polyorthoesters, polyphosphazenes, polyphosphoesters, certain polyhydroxyacids, polypropylfumerates, polycaprolactones, polyamides, poly(amino acids), polyacetals, polyethers, biodegradable polycyanoacrylates, biodegradable polyurethanes and polysaccharides. For example, specific biodegradable polymers that may be used include but are not limited to polylysine, poly(lactic acid) (PLA), poly(glycolic acid) (PGA), poly(caprolactone) (PCL), poly(lactide-co-glycolide) (PLG), poly(lactide-co-caprolactone) (PLC), and poly(glycolide-co-caprolactone) (PGC). Another exemplary degradable polymer is poly(beta-amino esters), which may be suitable for use in accordance with the present application.

In general, any layer within a particle described herein can have a thickness independently and within any ranges. In some embodiments, some or all layers have the same thickness or within the same range.

A layer on a substrate can have an average thickness in various ranges. In some embodiments, an averaged thickness is about or less than 5 μm, 1 μm, 800 nm, 500 nm, 400 nm, 300 nm, 200 nm, 100 nm, 90 nm, 80 nm, 70 nm, 60 nm, 50 nm, 40 nm, 30 nm, 20 nm, 15 nm, 10 nm, 5 nm, 1 nm, 0.5 nm, or 0.1 nm. In some embodiments, an averaged thickness is about or greater than 5 μm, 1 μm, 800 nm, 500 nm, 400 nm, 300 nm, 200 nm, 100 nm, 90 nm, 80 nm, 70 nm, 60 nm, 50 nm, 40 nm, 30 nm, 20 nm, 15 nm, 10 nm, 5 nm, 1 nm, 0.5 nm, or 0.1 nm. In some embodiments, an averaged thickness is in a range from about 0.1 nm to about 5 μm, about 0.5 nm to about 200 nm, about 5 nm to about 50 nm or about 10 to about 30 nm. In some embodiments, an averaged thickness is in a range of any two values above.

In some embodiments, a layer can have or be modified to have one or more functional groups. Such functional groups (within or on the surface of a layer) can be used for association with any agents (e.g., detectable entities, targeting entities, or PEG). Such associated agents can be dopant entities, if associated (e.g., doped) within layers. For example, targeting entities and/or PEG can be associated within one or more layers comprising degradable polymers. When the degradable polymers degrade, the dopant entities can be exposed.

In some embodiments, the surface of an outer-most layer can be modified with reagents to add and/or modify the functional groups on the outer layer (e.g., compounds such as, but not limited to, mercaptosilanols, aminosilanols can be used to introduce sulfhydryl or amine groups, respectively, to silica, tantalia, etc.; or catechol-amines can be used to introduce cationic amine-functionality to titania, etc.; oxidizing the newly introduced sulfhydryl-group with hydrogen peroxide to generate anionic sulfonate-functionality can further chemically alter the introduced groups). Apart from changing the surface charge by introducing or modifying surface functionality, the introduction of different functional groups allows the conjugation of linkers (e.g., (cleavable or (bio-)degradable) polymers such as, but not limited to, polyethylene glycol, polypropylene glycol, PLGA, etc.), targeting/homing agents (e.g., such as, but not limited to, small molecules (e.g., folates, dyes, etc.), (poly) peptides (e.g., RGD, epidermal growth factor, chlorotoxin, etc.), antibodies, proteins, etc.), contrast/imaging agents (e.g., fluorescent dyes, (chelated) radioisotopes (SPECT, PET), MR-active agents, CT-agents), therapeutic agents (e.g., small molecule drugs, therapeutic (poly)peptides, therapeutic antibodies, (chelated) radioisotopes, etc.), or combinations thereof.

Dopant Entity

In accordance with some embodiments described herein, dopant entities can be associated within one or more layers of a particle. In some embodiments, dopant entities are attached directly or indirectly to layers. In some embodiments, dopant entities are distributed within layer; in some embodiments, dopant entities are discretely localized within layers.

In general, dopant entities can be encapsulated independently within any possible distance from a substrate of a particle. Exemplary distance includes 5 µm, 1 µm, 800 nm, 500 nm, 400 nm, 300 nm, 200 nm, 100 nm, 90 nm, 80 nm, 70 nm, 60 nm, 50 nm, 40 nm, 30 nm, 20 nm, 15 nm, 10 nm, 5 nm, 1 nm, 0.5 nm, or 0.1 nm.

In some embodiments, dopant entities are positioned within a predetermined distance from the surface of a substrate or an adjacent layer. Such a distance in various embodiments can be about or less than 1 nm, 2 nm, 3 nm, 4 nm, 5 nm, 6 nm, 7 nm, 8 nm, 9 nm, 10 nm, 15 nm, 20 nm, 30 nm, 40 nm, 50 nm, 100 nm, 200 nm, 300 nm, 400 nm, or 500 nm. In some embodiments, a distance between a dopant entity and the surface of a substrate is a range of 2 nm to 5 nm, 5 nm to 10 nm, or 10 nm to 15 nm. In some embodiments, dopant entities can be in direct contact to the surface of a substrate or an adjacent layer.

In some embodiments, surface primers can be used after substrate synthesis. Exemplary surface primers include, but are not limited to, functionalized silica agents such as MPTMS and APTMS, or polymer (e.g., polyethyleneglycol-(PEG)-thiol).

In some embodiments, dopant entities have sufficient affinity for one or more components of a particle to permit displacement of a capping agent and/or to permit high density and/or close surface localized loading of the dopant entity(ies) into or onto the particle. A capping agent can be an entity that is displaceably associated with a substrate. Without wishing to be bound by any particular theory, it is noted here that, in some embodiments, capping agents can play an important role in substrate synthesis. In some embodiments, capping agents control the size and geometry of a substrate. In some embodiments, capping agents are present after synthesis as an adsorbed monolayer on the synthesized substrate. In some embodiments, capping agents are strongly adsorbed to the surface of a substrate. In some embodiments, capping agents provide stabilization and/or prevent aggregation of substrates. Exemplary capping agents include, but are not limited to, organic agents such as citrate, citric acid, ascorbic acid, ascorbate, palmitoyl ascorbate, tetrakis(hydroxymethyl)phosphonium chloride, and amino acids. In some such instances, some or all capping agents are ultimately removed from a substrate by surface primers. In contrast to traditional surface priming methods wherein capping agents are displaced by surface primers, in some embodiments of the present disclosure a capping agent itself is employed to enable substrate encapsulation.

In some embodiments, the dopant entity is embedded, coordinated to, or covalently bound to a layer (e.g., to a condensation layer or an encapsulant layer).

In some embodiments, the dopant entity can be associated with a layer (e.g., with a condensation layer or an encapsulant layer) via (bioorthogonal) click-chemistry.

In various embodiments, one or more layers can have one or more entities/agents (e.g., detectable entities, targeting entities, or PEG) doped within. In general, any entity of interest can be utilized as a dopant entity in accordance with the present invention. A single dopant entity (or a layer/substrate) can be susceptible to imaging in multiple modalities.

In some embodiments, a dopant entity is a detectable entity including, but not limited to, SE(R)RS-active agent, fluorochromes (e.g., near infrared (metal-enhanced fluorescence agent, 2-photon fluorescence agent), MRI agents, photoacoustic-active dyes, upconverting materials, positron emission tomography (PET) tracers, single photon emission tomography (SPECT) tracers, computed tomography (CT) agents, X-Rays agents, ultrasound (US) agents and combinations thereof.

Referring to FIG. 13 again, layers can be doped with compounds/materials such as, but not limited to, SER(R)S-active dyes, (near infrared) fluorescent dyes, luminescent compounds, photoacoustic-active dyes, upconverting materials (e.g., consisting of materials from the group of the rare-earth metals and/or transition metals), (laser) pumping materials (e.g., including, but not limited to, materials from the group of the rare-earth metal- and/or transition metal-based compounds), "slow light"-inducing materials (e.g., praseodymium-based compounds), MRI-active materials (e.g., including, but not limited to, rare-earth metals and/or transition metals such as gadolinium, manganese, iron(-oxides)). In some embodiments, at least one layer is doped with, for instance, a SERRS-active dye (indicated by "1") and at least one other layer is doped with, for instance, a near infrared fluorescent dye (indicated by "2") (left). In certain embodiments, some layers do not contain dopants but serve as spacers and/or separators between two dopant-containing shells (middle). Layers can additionally be doped with therapeutic agents (indicated by the stars) including, but not limited to, (radiolabeled-)small molecule-, chelate-, peptide-, protein-, antibody, RNA, DNA, aptamer-based compounds/materials (right), and combinations thereof.

SE(R)RS-Active Agents

In some embodiments, a dopant is or comprises a dye, for example, a resonance dye. A dopant entity can be or comprise an agent useful in Raman spectroscopy (e.g., SE(R)RS-active agents). Exemplary dopant entities include, but are not limited to, those agents described in the art such as in U.S. Pat. Nos. 5,306,403, 6,002,471, and 6,174,677, the contents of which are incorporated herein by reference in their entirety.

In some particular embodiments, a dopant entity is SE(R)RS- and/or photoacoustic active agent(s). In some particular embodiments, a high density of a SE(R)RS-active agent located close to a substrate contributes to unprecedented Raman sensitivity achieved by a particle described herein. SE(R)RS-active agents generally benefit from signal intensity enhancement in the proximity of a metal surface. In accordance with the present disclosure, a skilled artisan in the art would be capable to choose a SE(R)RS-active agent, to achieve chemical enhancement and/or electromagnetic enhancement, considering factors such as substrate materials, substrate configurations, layer material, etc. Such a SE(R)RS-active agent can have a charge transfer effect, from a metal to the molecule, or from the molecule to the metal.

A SE(R)RS-active agent refers to a molecule that is capable of generating a SERS or SE(R)RS spectrum when appropriately illuminated. Non-limiting examples of SE(R)RS-active agents include phthalocyanines such as methyl, nitrosyl, sulphonyl and amino phthalocyanines, naphthalocyanines, chalcogen-based dyes, azomethines, cyanines, squaraines, and xanthines such as the methyl, nitro, sulphano and amino derivatives. Each of these may be substituted in any conventional manner, giving rise to a large number of useful labels. It is noted that the choice of a SE(R)RS-active agent can be influenced by factors such as the resonance frequency of the molecule, the resonance frequency of other molecules present in a sample, etc.

Typically, detecting a SE(R)RS signal involves using incident light from a laser. The exact frequency chosen will depend on the SE(R)RS-active agent, and metal surface. Frequencies in visible or near-infrared spectrum tend, on the whole, to give rise to better surface enhancement effects for noble metal surfaces such as silver and gold. However, it is possible to envisage situations in which other frequencies, for instance in the ultraviolet range might be used. The selection and, if necessary, tuning of an appropriate light source, with an appropriate frequency and power, will be well within the capabilities of one of ordinary skill in the art, particularly on referring to the available SE(R)RS literature.

The Raman enhancement generally is proportional to the density of a SE(R)RS-active agent associated (e.g., adsorbed) on a metal surface. A surprisingly high density of a SE(R)RS-active agent adsorbed on a substrate surface in accordance with the present disclosure may contribute to the superior sensitivity of particles disclosed herein.

Fluorescent Agents

In some embodiments, a dopant entity is or comprises a fluorescent dye/agent (e.g., near infrared (NIR) fluorescent dye). For example, fluorescent dyes/agents including, but not limited to, polymethines, cyanines, (na)phthalocyanines, porphorines, merocyanines, (pe)rylene (bisimides), squaraines, anthocyanins, phycocyanins, bodipys, rotaxanes, rhodamines, certain organometallic complexes, can be used in accordance with the present invention.

In some embodiments, a fluorescent dye/agent has a predetermined distance from a substrate by means of synthesis method described therein. An exemplary particle doped with a near infrared (NIR) fluorescent dye and other agents was demonstrated in Examples below.

MRI Agents

In some embodiments, a dopant entity is or comprises an MRI agent. In some embodiments, the amount or number of MRI agents associated with a layer can be about 1 to 10,000,000 MRI agents or about 5000 to 500,000 MRI agents. See US Patent Application Publication No. 20120179029, the contents of which are incorporated by references.

Some embodiments of a MRI agent can be Gd(-salts), iron oxide, paramagnetic chemical exchange saturation transfer (CEST) agents, $^{19}F$ active materials, manganese, melanin, or a substance that shortens or elongates T1 or T2 and a combination thereof. In certain embodiments, a Gd MRI agent can be a compound such as DOTA-Gd, DTPA-Gd, Gd within a polymeric chelator, and Gd immobilized by negative charges on a layer. In certain embodiments, an iron oxide MRI agent can be a compound such as a small paramagnetic iron oxide (SPIO) or an ultrasmall SPIO with or without a dextran or other stabilizing layer. In certain embodiments, a paramagnetic CEST MRI agent can be a compound such as lanthanide complexes.

In some embodiments, MRI agents can be linked to a layer via a linkage such as a maleimide linkage, NHS ester, click chemistry, or another covalent or non-covalent approach or a combination thereof. In some embodiments, MRI agents can also be loaded without addition of any exogenous agent, i.e., only layer(s) and MRI agent.

Alternatively or in addition to MRI agents, one or more other agents can be associated with a particle. Exemplary diagnostic agents including a PET (e.g., $^{18}F$, $^{64}Cu$, $^{11}C$, $^{13}N$, $^{15}O$, and the like), SPECT (e.g., $^{99}Tc$, $^{67}Ga$, $^{192}Ir$ and the like), fluorochrome (e.g., Alexa 647, Alexa 488 and the like), radio nuclide (e.g., alpha-emitting radionuclides (e.g., At-211, Bi-212, Bi-213, Ra-223, and Ac-225), beta-emitting radionuclides (e.g., Cu-67, Y-90, Ag-111, I-131, Pm-149, Sm-153, Ho-166, Lu-177, Re-186, and Re-188)), and the like, can be associated with a particle and be detected using appropriate detection systems. In certain embodiments, the use of a radionuclide can be used to induce signal via Cerenkov radiation.

In addition to detectable entities or alternatively, particles described herein can be prepared with dopant entities that are agents intended for administration or delivery. In some embodiments, such an agent remains associated with the particle after administration of the particle; in some embodiments, such an agent is released or otherwise dissociated from the particle after administration.

Any of a wide range of dopant entities may be used in accordance with the present invention. Exemplary dopant entities may include, but are not limited to, therapeutic agents and/or imaging agents. For example, dopant entities may be or comprise any therapeutic agents (e.g., antibiotics, NSAIDs, angiogenesis inhibitors, neuroprotective agents), cytotoxic agents, diagnostic agents (e.g., contrast agents; radionuclides; and fluorescent, luminescent, and magnetic moieties), targeting agents, prophylactic agents (e.g., vaccines), and/or nutraceutical agents (e.g., vitamins, minerals, etc.), or other substances (e.g., salt) that may be suitable for introduction to biological tissues, including pharmaceutical excipients and substances for cosmetics, and the like.

Targeting Agents

An agent can be a targeting agent (e.g., a chemical or biological agent) having an affinity for a target in the living host, where the agent is associated with a particle (e.g., within a layer of the particle or on the surface of a layer). In some embodiments, a particle can be used to image, detect, study, monitor, evaluate, and/or screen a disease, condition, or related biological event corresponding to the target.

In some embodiments, a targeting agent can function to cause a particle to interact with a molecule(s). In some embodiments, a targeting agent can have an affinity for a cell, a tissue, a protein, DNA, RNA, an antibody, an antigen, and the like, that may be associated with a condition, disease, or related biological event, of interest. In some embodiments, a targeting agent can function to target specific DNA, RNA, and/or proteins of interest. In some embodiments, a targeting agent can include, but is not limited to, polypeptides (e.g., proteins such as, but not limited to, antibodies (monoclonal or polyclonal)), antigens, nucleic acids (both monomeric and oligomeric), polysaccharides, sugars, fatty acids, steroids, purines, pyrimidines, ligands, aptamers, small molecules, ligands, or combinations thereof, that have an affinity for a condition, disease, or related biological event or other chemical, biochemical, and/or biological events of the condition, disease, or biological event. In some embodiments, a targeting agent can include: sequence-specific DNA oligonucleotides, locked nucleic acids (LNA), and peptide nucleic acids (PNA), antibodies, and small molecule protein receptors.

Other Agents

In accordance with the present disclosure, a particle can include one or more agents for delivery after administration/implantation. Such an agent may be or comprise small molecules, large (i.e., macro-) molecules, or any combinations thereof. Additionally or alternatively, an agent can be a formulation including various forms, such as liquids, liquid solutions, gels, hydrogels, solid particles (e.g., microparticles, nanoparticles), or combinations thereof.

In representative, non-limiting, embodiments, an agent can be selected from among amino acids, vaccines, antiviral agents, nucleic acids (e.g., siRNA, RNAi, and microRNA agents), gene delivery vectors, interleukin inhibitors, immunomodulators, neurotropic factors, neuroprotective agents, antineoplastic agents, chemotherapeutic agents, polysaccharides, anti-coagulants, antibiotics, analgesic agents, anesthetics, antihistamines, anti-inflammatory agents, vitamins and/or any combination thereof. In some embodiments, an agent may be selected from suitable proteins, peptides and fragments thereof, which can be naturally occurring, synthesized or recombinantly produced.

In some embodiments, an agent is or comprises a biologic. Examples of biologics including, but are not limited to, monoclonal antibodies, single chain antibodies, aptamers, enzymes, growth factors, hormones, fusion proteins, cytokines, therapeutic enzymes, recombinant vaccines, blood factors, and anticoagulants. Exemplary biologics suitable for use in accordance with the present disclosure are discussed in S. Aggarwal, *Nature Biotechnology*, 28:11, 2010, the contents of which are incorporated by reference herein.

In some embodiments, compositions and methods in accordance with the present application are particularly useful to deliver one or more therapeutic agents.

In some embodiments, a therapeutic agent is a small molecule and/or organic compound with pharmaceutical activity. In some embodiments, a therapeutic agent is a clinically-used drug. In some embodiments, a therapeutic agent is or comprises an anti-cancer agent, antibiotic, antiviral agent, anesthetic, anticoagulant, inhibitor of an enzyme, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, anti-glaucoma agent, neuroprotectant, angiogenesis inhibitor, etc.

Exemplary anticancer agents include, but are not limited to, a cytokine, a chemokine, a growth factor, a photosensitizing agent, a toxin, an anti-cancer antibiotic, a chemotherapeutic compound, a radionuclide, an angiogenesis inhibitor, a signaling modulator, an anti-metabolite, an anti-cancer vaccine, an anti-cancer oligopeptide, a mitosis inhibitor protein, an antimitotic oligopeptide, an anti-cancer antibody, an anti-cancer agent, antibiotic, an immunotherapeutic agent, hyperthermia or hyperthermia therapy, a bacterium, radiation therapy and any combination of such agents. In some examples, an anticancer agent is cisplatin, carboplatin, gemcitabine, irinotecan, an anti-EGFR antibody, an anti-VEGF antibody and any combinations thereof.

A therapeutic agent used in accordance with the present application can be or comprise an agent useful in combating inflammation and/or infection. A therapeutic agent may be an antibiotic. Exemplary antibiotics include, but are not limited to, β-lactam antibiotics, macrolides, monobactams, rifamycins, tetracyclines, chloramphenicol, clindamycin, lincomycin, fusidic acid, novobiocin, fosfomycin, fusidate sodium, capreomycin, colistimethate, gramicidin, minocycline, doxycycline, bacitracin, erythromycin, nalidixic acid, vancomycin, and trimethoprim. For example, β-lactam antibiotics can be ampicillin, aziocillin, aztreonam, carbenicillin, cefoperazone, ceftriaxone, cephaloridine, cephalothin, cloxacillin, moxalactam, penicillin G, piperacillin, ticarcillin and any combination thereof. Other anti-microbial agents such as copper may also be used in accordance with some embodiments of the present invention. For example, antiviral agents, anti-protazoal agents, anti-parasitic agents, etc. may be of use. Additionally or alternatively, a therapeutic agent may be an anti-inflammatory agent.

A therapeutic agent may be a mixture of pharmaceutically active agents. For example, a local anesthetic may be delivered in combination with an anti-inflammatory agent such as a steroid. Local anesthetics may also be administered with vasoactive agents such as epinephrine. In some embodiments, an antibiotic may be combined with an inhibitor of the enzyme commonly produced by bacteria to inactivate the antibiotic (e.g., penicillin and clavulanic acid).

In some embodiments, a therapeutic agent may include a therapeutic gene as known in the art. In some embodiments, a therapeutic agent is or includes a non-viral vector. Typical non-viral gene delivery vectors comprise DNA (e.g., plasmid DNA produced in bacteria) or RNA. In certain embodiments, a non-viral vector is used in accordance with the present invention with the aid of a delivery vehicle. Delivery vehicles may be based around lipids (e.g., liposomes) which fuse with cell membranes releasing a nucleic acid into the cytoplasm of the cell. Alternatively or alternatively, peptides or polymers may be used to form complexes (e.g., in form of particles) with a nucleic acid which may condense as well as protect the therapeutic activity as it attempts to reach a target destination.

Uses and Applications

Provided are particles and methods that can be used in various applications including medical and non-medical applications. Non-medical (e.g., clinical) applications that could benefit from the herein described methods are, for instance, biomedical research methodologies (such as, but not limited to, cell tracking, cell sorting, western blotting), solar cells, quantum computing-based applications/methods, anti-counterfeit applications/methods, barcoding, optics, (nano)photonics.

Those skilled in the art will appreciate that design/structure of particles may be selected and/or include features adapted for a particular use. To give but a few examples, representative exemplary particles structures depicted in FIGS. 12-18 and/or described in Examples 4 and 5 can be particularly useful for in vivo imaging.

In some embodiments, compositions and methods described herein are useful for non-malignant diseases, such as, for example, Alzheimer's disease, Parkinson's disease, inflammatory diseases, autoimmune diseases, infectious diseases, and other non-malignant diseases.

In some embodiments, compositions and methods described herein are useful for malignant diseases. Particles described in some embodiments of the present disclosure can be used to image, detect, study, monitor, and/or evaluate, any malignant or atypical cells or tissues, including a condition or disease such as pre-cancerous tissue, cancer, or a tumor. In some embodiments, compositions and methods described herein are particularly useful for solid tumors. Exemplary solid tumors include, but are not limited to, malignant tumors of brain, lung, breast, ovary, stomach, pancreas, larynx, esophagus, testes, liver, parotid, biliary tract, colon, rectum, cervix, uterus, endometrium, kidney, bladder, prostate, thyroid, head and neck, melanomas, gliomas, neuroblastomas, neuroendocrine tumors, and the like.

In some embodiments, provided particles can be associated with a cell (e.g., located within a cell or attached to cell surface) for cell tracking.

Exemplary administrations of particles include but are not limited to oral, intravenous, sublingual (i.e., under a tongue), respiratory, or intraoperative administrations. It is recognized in the present application that provided particles and methods can be of particular interest in and surprisingly useful for detecting residual tumor in surgery.

In some embodiments, particles can be used to image, detect, study, monitor, evaluate, and/or screen a sample or subject (e.g., whole-body or a portion thereof). Embodiments of the present disclosure include methods that involve one or more of planning resection of a tumor, evaluating a tumor, intraoperatively guiding tumor resection, verifying margins in vivo or ex vivo, or the like. In some embodiments, provided methods can include a pre-operative and intra-operative procedure time frame and can also include the post-operative procedure time frame to study removed tissue. In some embodiments, provided methods can include administering an appropriate amount of a particle composition (e.g., an effective dose(s)) so that administered particles are detectable in or near a tumor for a few days to a week or ten days. If needed, larger doses can be administered to maintain a detectable amount of the particle in the tumor. Alternatively or additionally, multiple doses of a particle can be administered during the time frame of the procedure.

In some embodiments, for example including certain provided methods of evaluating a tumor, after administration, particles can be imaged during one or more of the pre-operative, intra-operative, and/or post-operative time frames and/or via one or more imaging modalities, for example through detection of an MRI signal, a photoacoustic signal, a Raman signal, and any combinations thereof. Each such signal can be included in an information set (e.g., signal, location of the signal, time of the signal, intensity of the signal, and the like, wherein one or more of these or a combination can be referred to as "data" as discussed below) that can be analyzed. An appropriate energy can be used to produce the photoacoustic and Raman signals, as described in more detail in U.S. Patent Application Publication No. 20120179029, the contents of which are incorporated herein by reference in their entirety.

In some embodiments, a MRI signal can be used to produce an image corresponding to one or more of: the localization of the whole tumor, macroscopic delineation of the whole tumor, and residual portions of the tumor. The first two can be measured or detected during the pre-operative time frame of the procedure, while the last is measured or detected during the post-operative time frame of the procedure. A MRI signal can be measured or detected using an MRI system such as 15 T, 11 T, 9.4 T, 7 T, 3 T, 1.5 T, or 0.5 T or less, which is well known in the art.

In some embodiments, a photoacoustic signal is used to produce an image corresponding to the tumor with deep tissue penetration (e.g., about 4 to 10 cm). A photoacoustic signal can be measured using a photoacoustic system described in U.S. Patent Application Publication No. 20120179029, the contents of which are incorporated herein by reference in their entirety.

In some embodiments, a Raman vibrational signal can be used as a guide to defining the tumor margins as well as produce an image of a portion of the brain (e.g., edges of transition from tumor to brain tissue). A Raman vibrational signal can be measured using a Raman system as described herein (e.g., raster scanning or point by point scanning).

In some embodiments, an MRI signal, a photoacoustic signal, and a Raman signal (or the corresponding information set), can be used to image and/or determine the location, relative position, and/or the presence of a particle at a particular location, of one or more of: the tumor and the tumor margins, during the operative procedure. The signals (or the corresponding information set) can be used alone or in combination at any given point during the procedure. Signals (or the corresponding information set) can all be used to facilitate a superior resection procedure since at certain points of the procedure a single type of particle can be used to obtain each type of signal. This is advantageous because repeated injection of contrast agents can show decreased efficacy and may induce toxicity.

In some embodiments, for example including in certain provided methods of planning resection of a tumor as an example, after administration, particles may be imaged during one or more of the pre-operative, intra-operative, and/or post-operative time frames and/or via one or more imaging modalities, for example utilizing MRI data, photoacoustic data, Raman data, and combinations thereof. Data can be obtained by appropriate processing of each type of signal received to produce an image or monitored although not processed into an image. In some embodiments, one or more types data can be used to visualize (e.g., image) the tumor. Two or more of the types of data can be combined to visualize (e.g., produce an image) of the tumor. Processing of the signals to produce data is known in the art (e.g., MRI data processing).

In some embodiments, a MRI data corresponds to one or more of: tumor localization and macroscopic delineation of the tumor. In some embodiments, an MRI data can be used to obtain the whole tumor in the pre-operative time frame as well as obtain intra-operative or post-operative data regarding any remaining tumor.

In some embodiments, photoacoustic data corresponds to a tumor with deep tissue penetration (e.g., about 5 to 10 cm deep into the subject). In some embodiments, photoacoustic data corresponds to the intra-operative time frame of the procedure.

In some embodiments, a Raman data corresponds to the tumor margins. In some embodiments, a Raman data corresponds to the intra-operative time frame of the procedure and can also be used in the post-operative time frame of the procedure.

In some embodiments, MRI data, photoacoustic data, and Raman data can be used to determine the location of one or more of: the tumor and the tumor margins, during an operative procedure. The data (of each type, e.g., MRI data, photoacoustic data, and/or Raman data) can be used alone or in combination at any given point during the procedure. The data can all be used to facilitate a superior resection procedure since at certain points of the procedure a single type of particle can be used to obtain each type of data. This is advantageous because each of the three modalities has one or more complementary strengths such as greater depth penetration, greater spatial resolution, greater sensitivity, and greater specificity.

In some embodiments, a radiotracer can cause the emission of a Cerenkov signal. In some embodiments, a radiotracer can induce a secondary Cerenkov induced fluorescence signal, due to the presence of both the radiotracer and, for example, a fluorochrome within the same particle. In some embodiments, a provided particle comprises at least two imaging modalities wherein the sensitivity dependence as a function of depth below a given surface is different for the two modalities, such that the ratio of the signals generated by the modalities varies proportionately with depth. Calibration of this ratio can enable determination of particle location in three dimensions for tomographic applications.

In general, in some embodiments, the present invention provides methods of administering particles to a subject (e.g., a subject having a tumor or other entity for detection and/or removal) and/or imaging administered particles. In some embodiments, administered particles are susceptible to and/or imaged with a plurality of different imaging modalities, for example, selected from the group consisting of SE(R)RS, MRI, PET, SPECT, CT, X-ray, ultrasound, photoacoustic detection, Raman spectroscopy, and any combinations thereof. In some embodiments, different imaging modalities are utilized substantially simultaneously; in some embodiments, different imaging modalities are utilized at one or more different times and/or in one or more different contexts (e.g., pre-operative, intra-operative, and/or post-operative). In some embodiments, at least one imaging modality is utilized at a plurality of different times and/or in a plurality of different contexts.

Although methods described above are directed to tumors, other tissue types can be substituted for the tumor. For example, pre-cancerous or cancerous cells or even noncancerous cells such as inflammation or infection can be treated in the similar way.

Some embodiments of the set-ups that may be used with embodiments of the present invention may include a computer which executes software (e.g., non-transitory computer readable medium) that controls the operation of one or more instruments, and/or that processes signals or other obtained data. The software may include one or more modules recorded on machine-readable media such as magnetic disks, magnetic tape, CD-ROM, and semiconductor memory, for example. The machine-readable medium may be resident within the computer or can be connected to the computer by a communication link (e.g., access via internet link). However, in alternative embodiments, one can substitute computer instructions in the form of hardwired logic for software, or one can substitute firmware (i.e., computer instructions recorded on devices such as PROMs, EPROMS, EEPROMs, or the like) for software. The term machine-readable instructions as used herein is intended to encompass software, hardwired logic, firmware, object code and the like.

The computer can be a general purpose computer. The computer can be, for example, an embedded computer, a personal computer such as a laptop or desktop computer, a mobile device, or another type of computer, that is capable of running the software, issuing suitable control commands, and/or recording information in real-time. The computer may include a display for reporting information to an operator of an instrument (e.g., displaying an acquired image), a keyboard for enabling the operator to enter information and commands, and/or a printer for providing a print-out, or permanent record, of images or measurements made by the system and for printing results. In certain embodiments, some commands entered at the keyboard enable a user to perform certain data processing tasks. In certain embodiments, data acquisition and data processing are automated and require little or no user input after initializing the system.

Embodiments described herein can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and methods described herein), or any combination of such back end, middleware, or front end components. The components of the system can be interconnected by any form or medium of digital data communication (e.g., a communication network). Examples of communication networks include a local area network (LAN), a wide area network (WAN), and the Internet. Embodiments utilized herein may utilize cloud-based computing.

EXEMPLIFICATION

The following examples demonstrate the development of multimodal (e.g., theranostic) nanoparticle that enables pre-surgical staging and planning, image-guided surgery, intra-operative tumor delineation (macroscopic) and residual single tumor cell detection (microscopic), all with one single intravenous injection, enabled by a novel synthesis strategy that allows controlled multilayer silica formation.

Example 1: Synthesis of SE(R)RS Particles

Gold nanostar-shaped substrates were synthesized by rapidly adding 20 mM $HAuCl_4$ to 40 mM ascorbic acid at 4° C. The as-synthesized ascorbate-stabilized gold nanostars (~75 nm, 1 nM) were collected by centrifugation (3,500×g, 15 min) and dialyzed overnight. The dialyzed gold nanostars were coated with dye-embedded silica via a typical Stöber method. In brief, the dialyzed gold nanostars were added to ethanol to which the resonant Raman dye, TEOS and ammonia were added and allowed to react for 1 hour. The particles were isolated by centrifugation (3,500×g, 15 min) and washed with ethanol. To enable PEGylation, the silica surface was modified with sulfhydryl-groups by heating the silica-coated nanostars for 1 hour at 72° C. in ethanol containing 1% (v/v) MPTMS. The nanostars were washed with ethanol to rid the MPTMS and redispersed in 10 mM MES buffer (pH 7.1) containing 1% (w/v) methoxy terminated (m)$PEG_{2000}$-maleimide. The maleimide-m$PEG_{2000}$ was allowed to react with the sulfhydryl-modified silica surface for 2 hours at ambient conditions. The PEGylated resonant Raman active nanostars were washed and redispersed in filter-sterilized 10 mM MES buffer (pH 7.3) and stored at 4° C. prior to injection. A resultant particle is illustrated in FIG. 1.

A SE(R)RS particle is unique in several ways, including as discussed below. 1) It has the highest detection sensitivity of any similar particles reported worldwide. 2) It allows visualizing tumors without the need for a specific targeting moiety on its surface, relying on the "enhanced permeability and retention" (EPR) effect. 3) It has a unique "fingerprint" Raman spectrum allowing detection with unequivocal specificity. 4) It combines a whole-body 3D imaging method with an ultra-high sensitivity detection method for optimal identification of tumor margins. 5) It becomes stably trapped within the tumors, which allows pre-operative staging and intraoperative resection with one single intravenous injection. 6) Rigorous toxicity evaluations of very similar gold-silica-based particles have found them to be safe in vivo.

Example 2: Characterization

Figure 2:
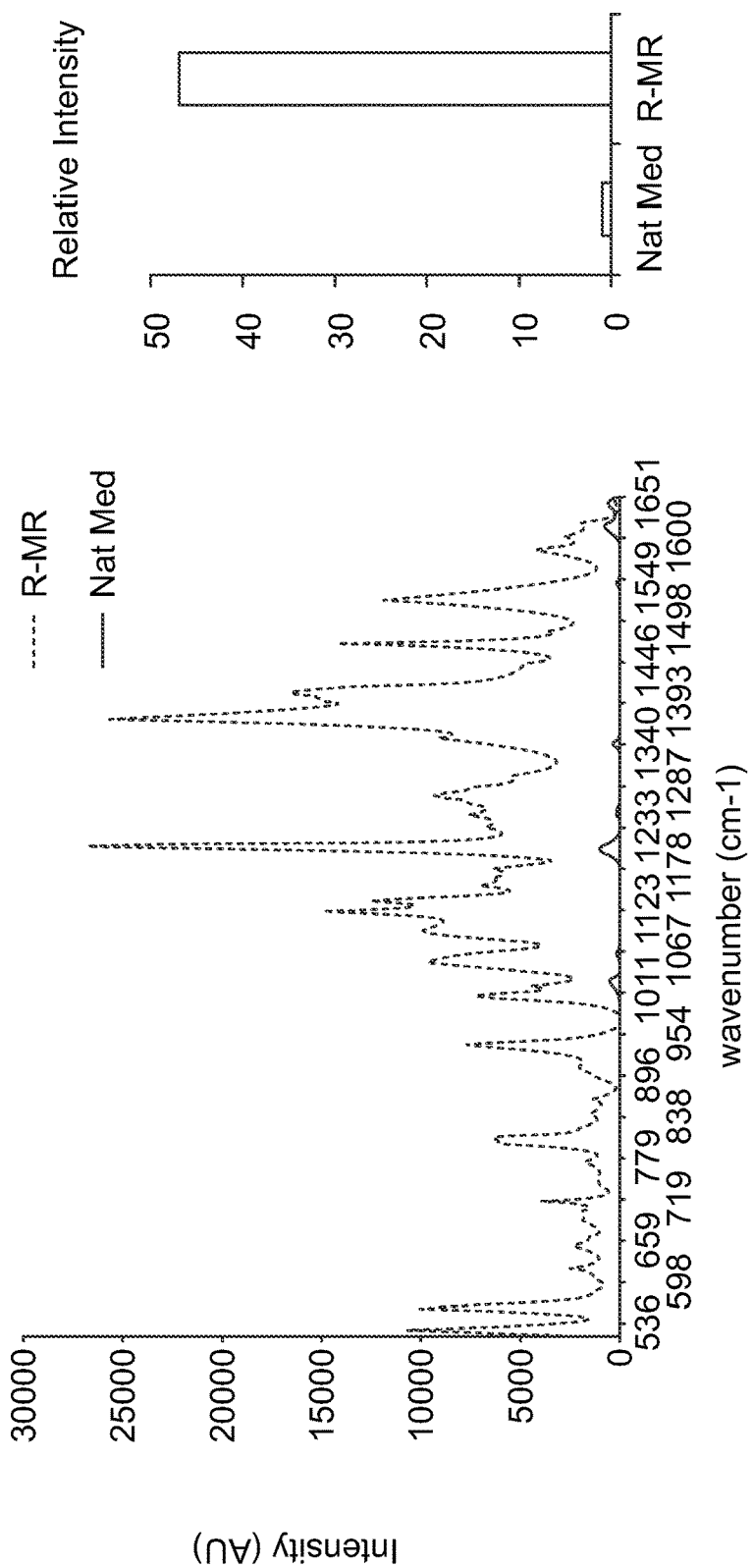
FIG. 2 illustrates direct comparison of the Raman spectral intensity of the SE(R)RS particles to the particles illustrated in Kircher et al., (2012) *Nat Med* 18 (5):829-834 currently considered to be the Raman gold standard. As shown in the bar graph, the SE(R)RS particles are 47-times more intense than the particles previously illustrated.

Ultra-High Sensitivity:

As shown in FIG. 2, the SE(R)RS particles synthesized in Example 1 were characterized by transmission electron microscopy (TEM; JEOL 1200EX, USA), size distribution and concentration were determined by nanoparticle tracking analysis (NTA; Nanosight, UK). Raman activities of equimolar amounts of particles were determined on a Renishaw InVIA Raman microscope equipped with a 300 mW 785 nm (near-IR) diode laser and a 1-inch charge-coupled-device detector for a spectral resolution of $1.07$ $cm^{-1}$. The Raman spectra were analyzed with WiRE 3.4 software (Renishaw, UK).

Figure 3:
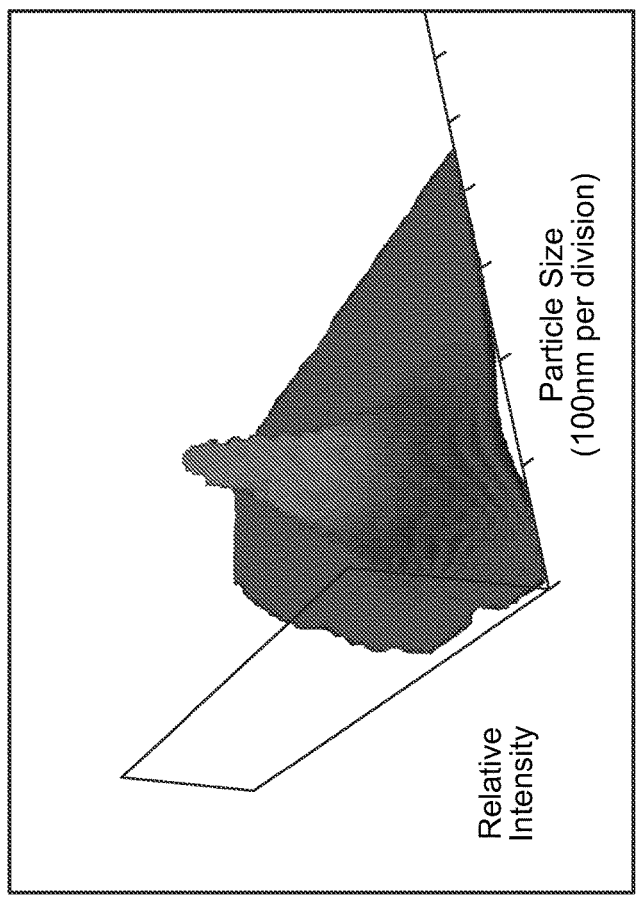
FIG. 3 displays the output of a typical Nanoparticle Tracking Analysis (NTA) scan. NTA enables accurate quantification of particle concentration and size distribution by locking into the light scattered from individual particles and tracing their paths in solution. The concentration is determined by simply counting the number of particles in a defined volume, while size is calculated from the Brownian motion using the Einstein-stokes equation. When combined with the complete morphological information provided by TEM, NTA allows for thorough characterization of the SE(R)RS particles.
Figure 4:
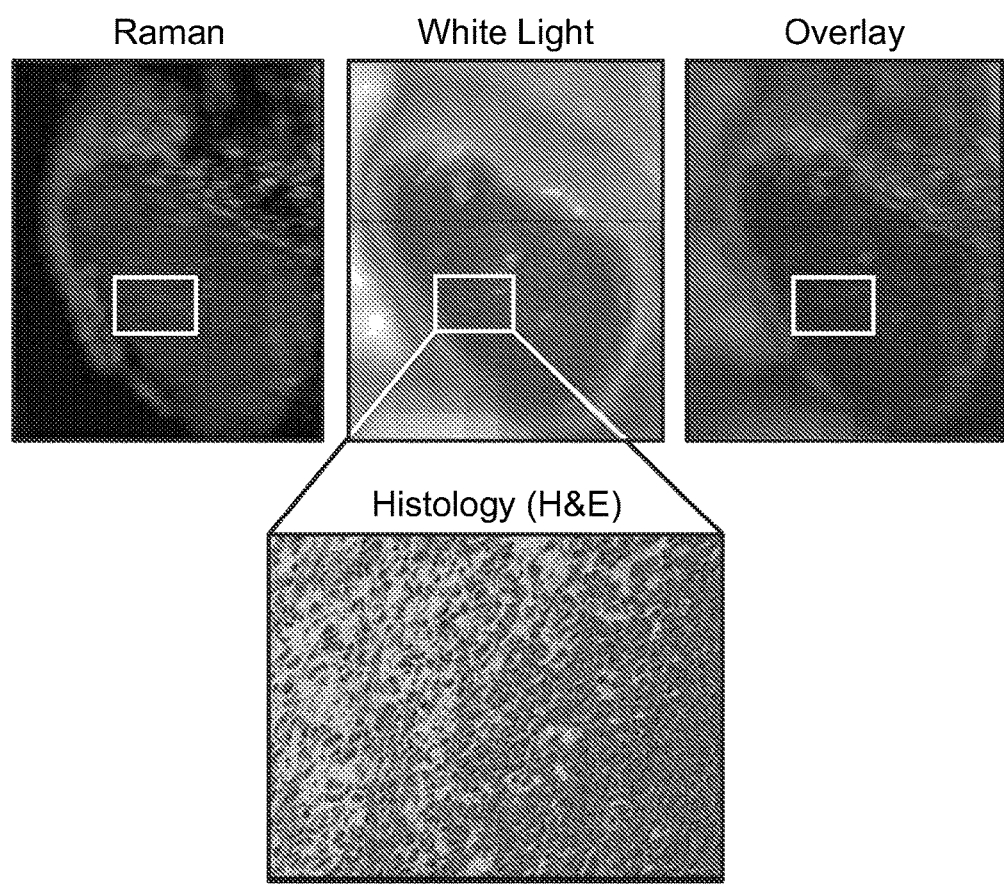
FIG. 4 shows a series of images of a mouse with dedifferentiated liposarcoma implanted in the flank.
Figure 5:
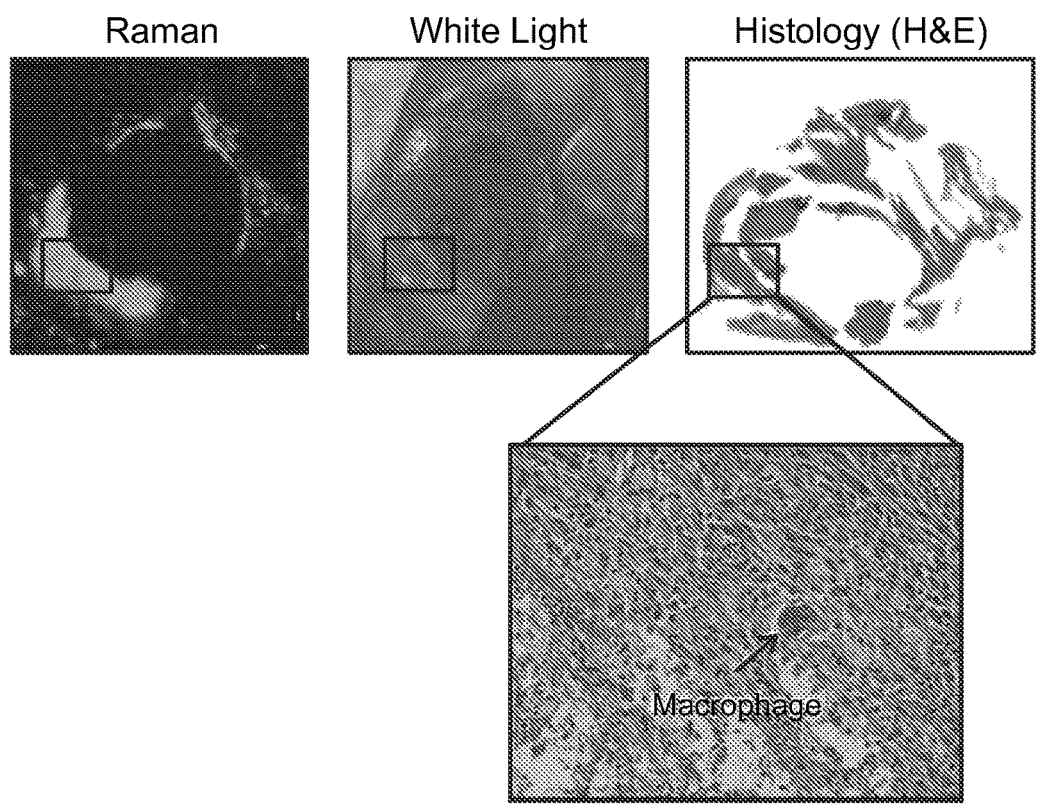
FIG. 5 shows a series of images of the same mouse as shown in FIG. 4, after resection of the bulk tumor by a surgeon using his unaided eye (blinded to Raman signal). Note that there is a residual rim of Raman signal in the resection bed around the resected tumor. Histological evaluation confirmed tumor in the locations of the Raman signal. Arrow, tumor-associated macrophage having engulfed SE(R)RS particles.
Figure 6:
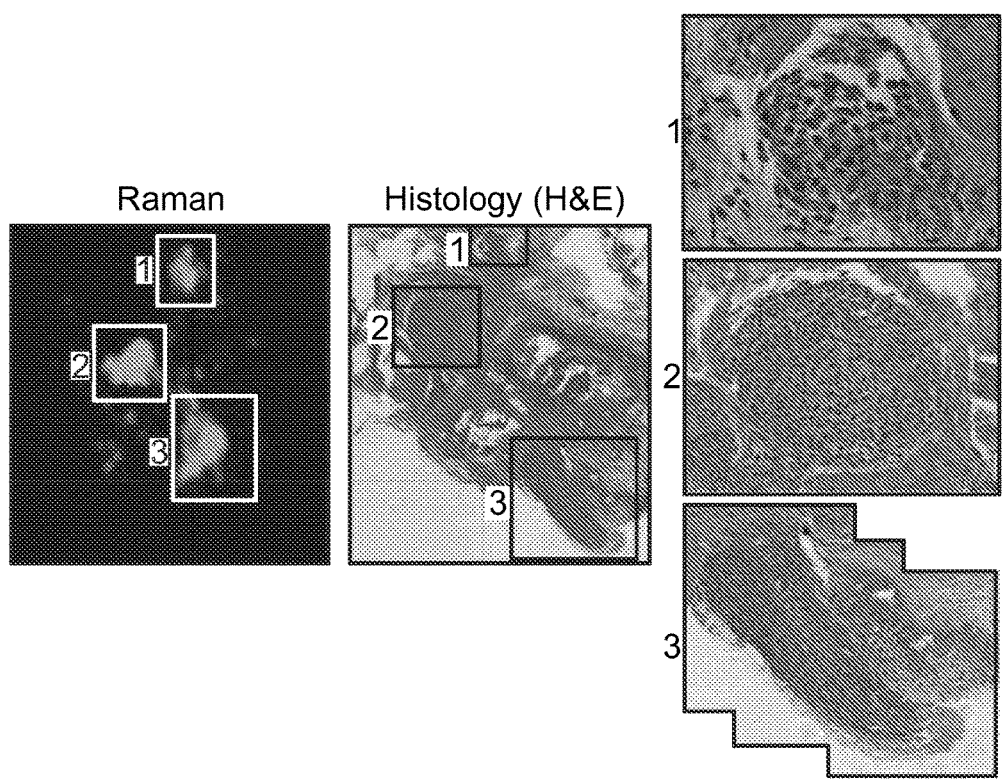
FIG. 6 shows images of a different mouse with liposarcoma, multiple small foci of Raman signal (1, 2 and 3) were found in the resection bed, after the bulk tumor had been resected by a surgeon using white light guidance only (blinded to Raman signal). As histological examination demonstrated, these foci of Raman signal precisely correlated to small tumor deposits (local micrometastases) 1 cm away from the main tumor. Magnified views are shown on the right.
Figure 7:
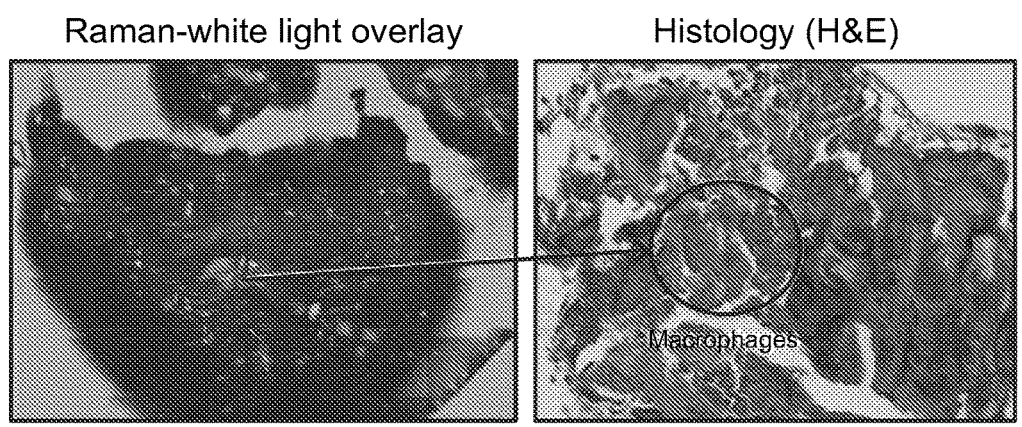
FIG. 7 shows images of the same mouse as that shown in FIG. 6 with sarcoma, multiple tiny foci of Raman signal are seen in the resection bed, after the bulk tumor had been resected by a surgeon using white light guidance only (blinded to Raman signal). As histological examination demonstrated, these foci of Raman signal represented tumor-associated macrophages.
Figure 8:
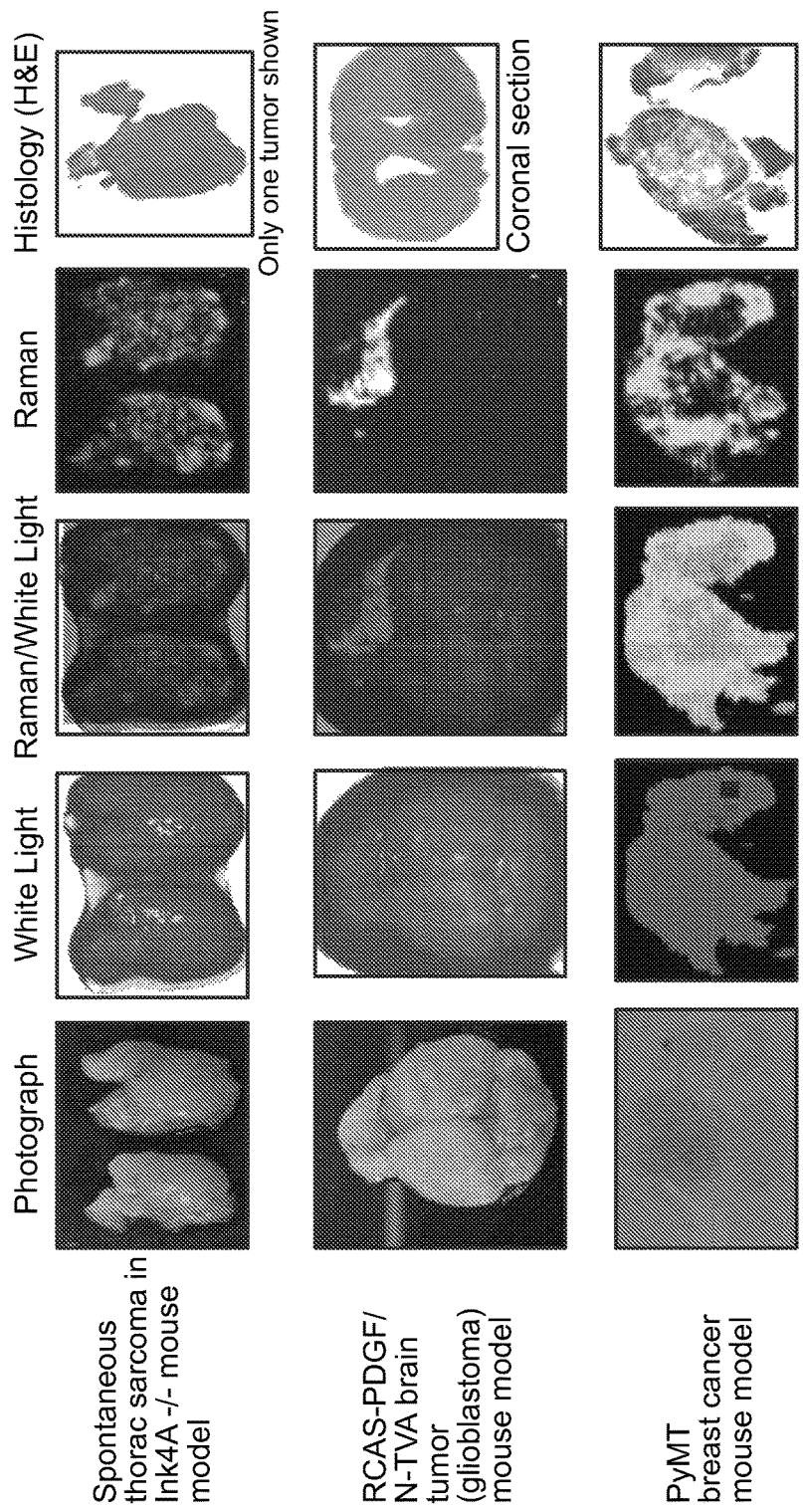
FIG. 8 demonstrates SE(R)RS particles are able to detect a variety of different tumors. Exemplary images are shown two spontaneous sarcomas in an Ink4A−/− mouse model, a brain tumor in the rcas/tv-a model, and a breast cancer in the PyMT model. In each tumor, there was excellent depiction of the tumor by the Raman signal.
Figure 9:
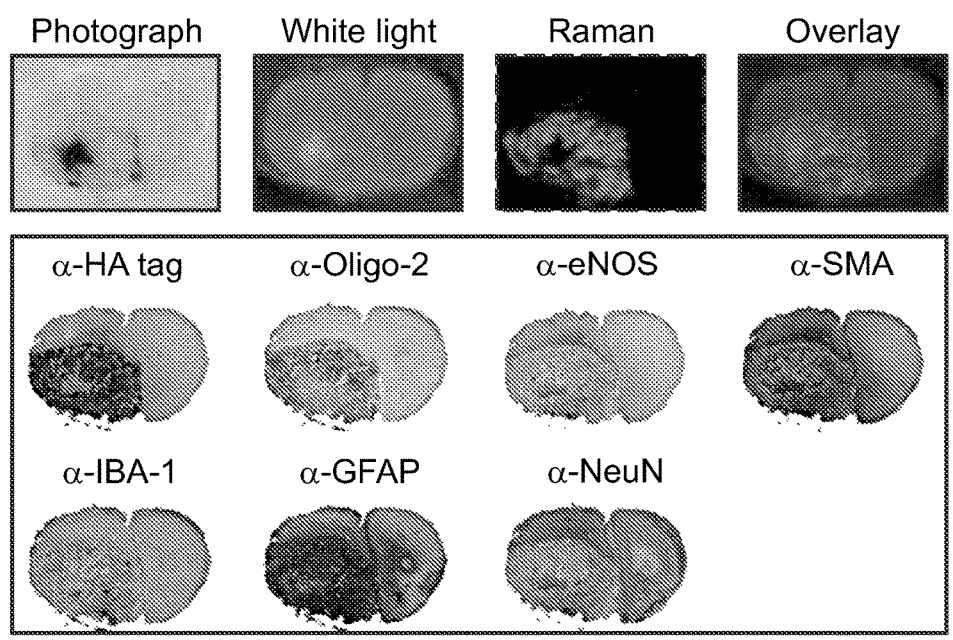
FIG. 9 demonstrates the ability of SE(R)RS particles to outline glioblastomas (rcas/tv-a model). Note the high degree of correlation of Raman signal with the presence of tumor cells (HA-tag, Oligo-2 positive staining).
Figure 10:
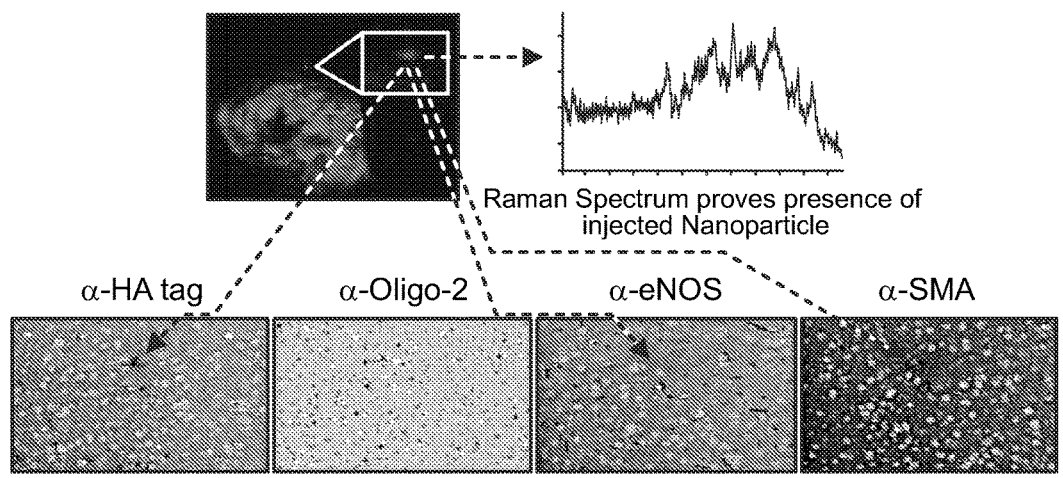
FIG. 10 demonstrates the ability of SE(R)RS particles to depict a single brain tumor cell (micrometastasis away from the main tumor). Insert in Raman image shows magnification of single Raman positive voxel. Raman spectrum proves presence of SE(R)RS particles. Histology confirms that this signal correlates to a signal brain tumor cell.

Nanoparticle Tracking Analysis (NTA):

As shown in FIG. 3, the size distribution of 1 pM of particles in water is determined by NTA.

Example 3: Animal Tests

Referring to FIGS. 4-10, tumor-bearing mice (Dedifferentiated LipoSarcoma model, PyMT-MMTV (fvb) transgenic breast cancer model, Hi-MYC transgenic prostate cancer model, RCAS/TV-a transgenic glioma model) were injected with 150 uL 2.5 nM SE(R)RS particles synthesized in Example 1. Animals were sacrificed 18 hours or later and were scanned for Raman activity on the above described system. Tumor, organs and lymph nodes were harvested and were additionally subjected to ex vivo imaging and were subsequently wax embedded. The embedded tissues were processed for histology (H&E staining, tumor marker staining, macrophage staining).

In Vivo-Ex Vivo Multimodal MRI-Raman-Histology Correlation:

As confirmed by the experimental results discussed below, SE(R)RS particles are able to depict the presence of tumor reliably and with microscopic precision in three different xenograft mouse sarcoma models (n=5 per model). The cells implanted in these mouse models are derived from actual human tumors. Mouse model #1 was a dedifferentiated liposarcoma model, mouse model #2 was a myxofibrosarcoma model, and mouse model #3 was a pleomorphic malignant fibrous histiocytoma (FMH) model. All 3 models are known to produce local tumor infiltration and satellite micrometastases around the primary tumor. Models #2 and #3 are known to also produce metastases to lung and bone, and the ability of the embodiments discussed herein to detect these distant metastases was also assessed. The tumor bearing mice were injected with the SE(R)RS particles (150 μl, 5 nM) intravenously; MRI was performed after 24 hours; then the animals were sacrificed and whole-body histological slicing was performed using a macrotome (same slice thickness as MRI); then these slices were imaged with a Raman microscope (Renishaw); and finally the same slices were processed histologically (H&E staining, tumor marker staining, macrophage staining) This allowed for assessing the precision of this multimodal SE(R)RS particle method, and for comparing, on the same slices, the Raman signal with the MRI signal and the presence of tumor cells as proven by histology.

Biodistribution and Dose Finding Studies in Mice:

In vivo PET-CT studies using SE(R)RS particles labeled with a PET tracer (zirconium-89, $^{89}Zr$) are conducted. The labeling of SE(R)RS particles with $^{89}Zr$ is performed in collaboration with the Lewis lab at MSKCC. $^{89}Zr$-SE(R)RS particles are injected intravenously into sarcoma bearing mice (n=3 for each tumor type above) and dynamic PET-CT imaging performed at 0, 1, 2, 4, 8, 12, 18, 24, 48 hours, 5 days, 7 days, 10 and 14 days. The PET data is provided A) an exact concentration of SE(R)RS particles within the tumors to allow calculation of the particle dosage used for aim 3, and B) a determination of the dynamics of intratumoral accumulation and retention of the SE(R)RS particles.

Testing of Raman-Guided Sarcoma Surgery in Dogs with Osteosarcoma:

Sarcomas can be resected in large animals using the SE(R)RS particles and a hand-held Raman detector. The hand-held scanner has specifications very similar to the Renishaw benchtop Raman microscope, including the use of a laser with the same wavelength in the near-infrared (785 nm) and the same laser power of 300 mW. The hand-held particle can be held directly against the tissue of interest, and indicates with sound (or optical signal, if preferred) when it detects the SE(R)RS particles described in accordance with some embodiments herein.

This aim is performed in collaboration with the Animal Medical Center (AMC) located on $62^{nd}$ Street in Manhattan (http://www.amcny.org). This animal clinic is a highly specialized institution that routinely performs surgery on animals, including sarcoma surgeries. The incidence of osteosarcoma in dogs is high.

Figure 11:
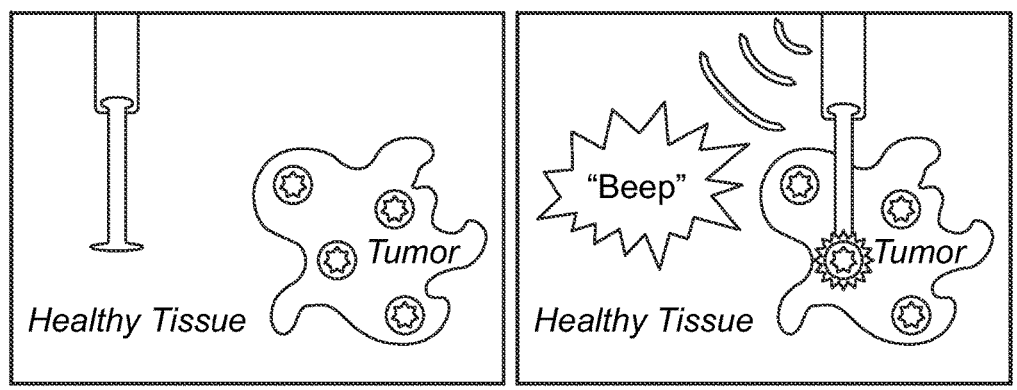
FIG. 11 illustrates a principle of hand-held Raman detection method as described in Examples.

The SE(R)RS particles are injected intravenously in the dogs (n=10). After 24 hours, animals are anesthetized with isofluorane anesthesia. After sterile prepping of the animals the tumors are surgically exposed and the bulk of the tumor that can be clearly identified by the surgeon with the naked eye is resected. When the resection has progressed close to tumor margin, the hand-held Raman particle is used to verify the presence of residual tumor and to search for the presence of local micrometastases in the surgical bed. If SE(R)RS particles are still present, the Raman scanner notifies the surgeon with a "beep" sound (see FIG. 11). The resection is then continued until all Raman positive foci are resected; the resected tissue specimen is sent for pathological evaluation (histology and tumor markers).

Example 4: Synthesis of Silica-Coated Particles

In some embodiments, dopant entities such as, but not limited to, SE(R)RS- and/or photoacoustic-active dyes, can be placed in a first condensation layer that extends for example up to 10 nm from a substrate. A second "buffer" condensation layer with a thickness of 5 nm can be layered on top of the first doped condensation layer. A third condensation layer doped with, but not limited to, a (near) infrared fluorescent dye, can be layered on the second layer, thus extending from 15 nm from the substrate up to, for instance, 100 nm. This example illustrates how the enhancement of each dopant entity can be optimized with the method described herein that allows precise control of layer thickness of multiple layers. For example, it prevents unwanted effects such as quenching of fluorescence, which would occur if a (near infrared) fluorescent dye would be located too close to the substrate, and reduced Raman enhancement if the Raman dye is located too far away from the substrate.

Figure 15:
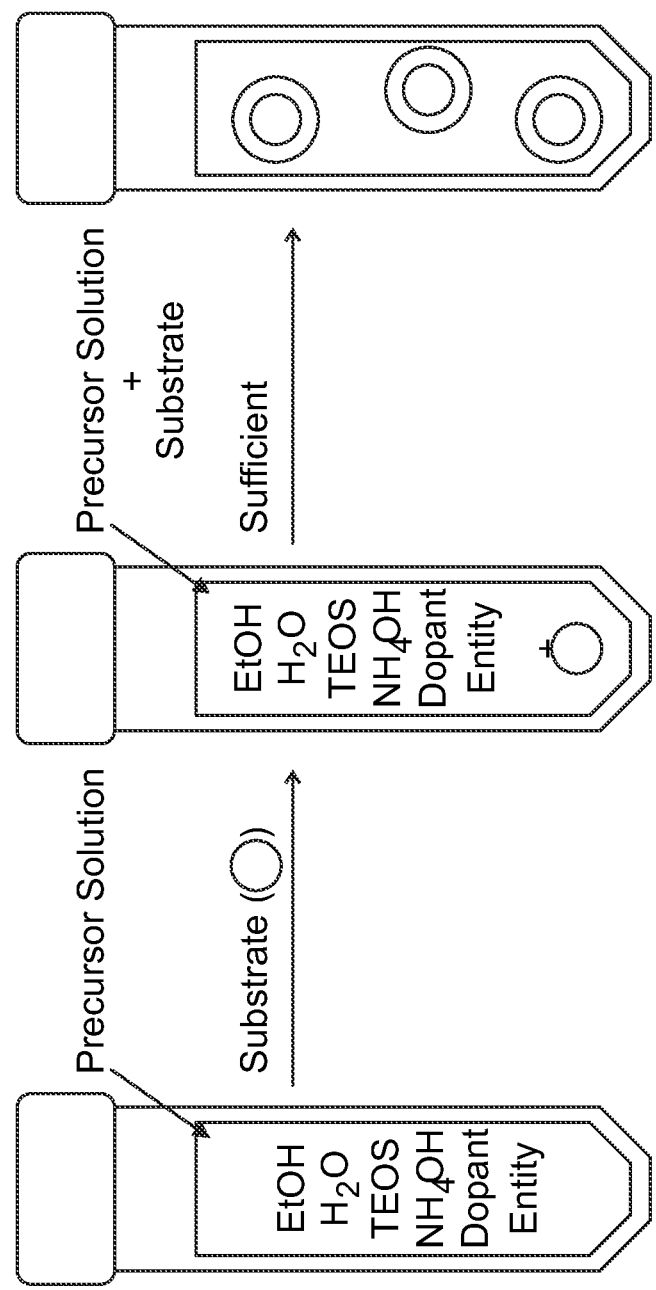
FIG. 15 is a schematic of preparing a particle with a silica condensation layer and a dopant entity in accordance with some embodiments of the present invention.

Similar to Example 1, gold substrates were synthesized by rapidly adding $HAuCl_4$ to ascorbic acid at 4° C. as known in the art. The as-synthesized ascorbate-stabilized gold substrates were collected by centrifugation and dialyzed overnight. The dialyzed gold substrates were coated with dye-embedded silica via a typical Stöber method. In brief, the dialyzed gold substrates were added to ethanol to which the resonant Raman dye, TEOS, ammonia and DI water were added and allowed to react for less than 1 hour. The particles were isolated by centrifugation (3,500×g, 15 min) and washed with ethanol. A schematic of the particle preparation is shown in FIG. 15.

A series of silica-coated particles were prepared using various amounts of DI water during the Stöber synthesis. Referring to FIG. 14, tunable ultrathin silica shells were demonstrated. By adjusting the water content, the silica shell thickness can be accurately tuned, which enables the incorporation of multiple dopant entities in accordance with the present disclosure.

Particles coated with a silica layer can be further coated with other silica layers by repeating the Stöber synthesis.

Figure 16:
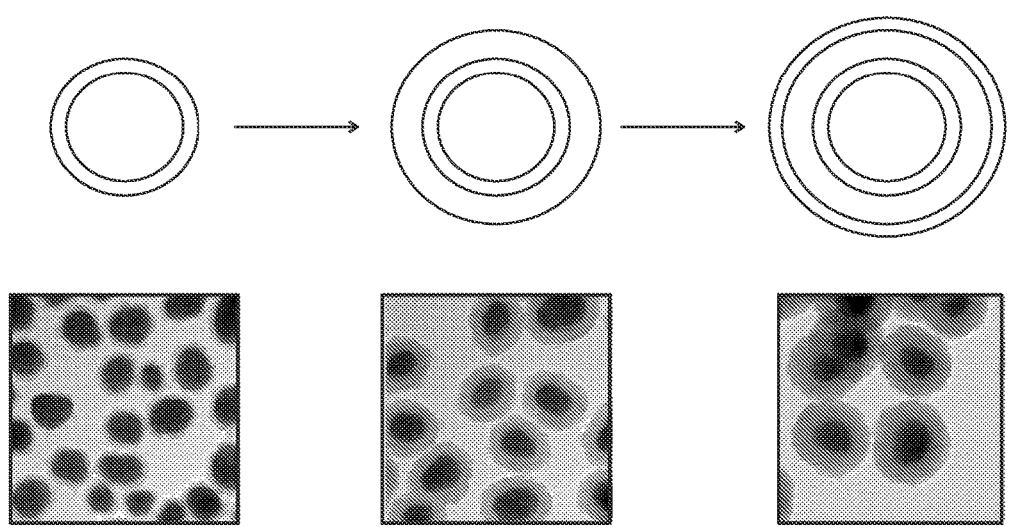
FIG. 16 includes a series of schematics and corresponding Transmission Electron Microscopy (TEM) images of exemplary particles illustrating the layering of different modalities in accordance with some embodiments of the present invention.

Exemplary particles are illustrated in FIG. 16. The first layer is a Surface-Enhanced Resonance Raman Scattering (SERRS)-layer, the second is a "buffer"-layer that separates the SERRS-layer from the third, near infrared (NIR) fluorescent layer. Inserts show actual layering as imaged by Transmission Electron Microscopy (TEM; scale bar=20 nm).

Example 5: Optical Characterization

Figure 17:
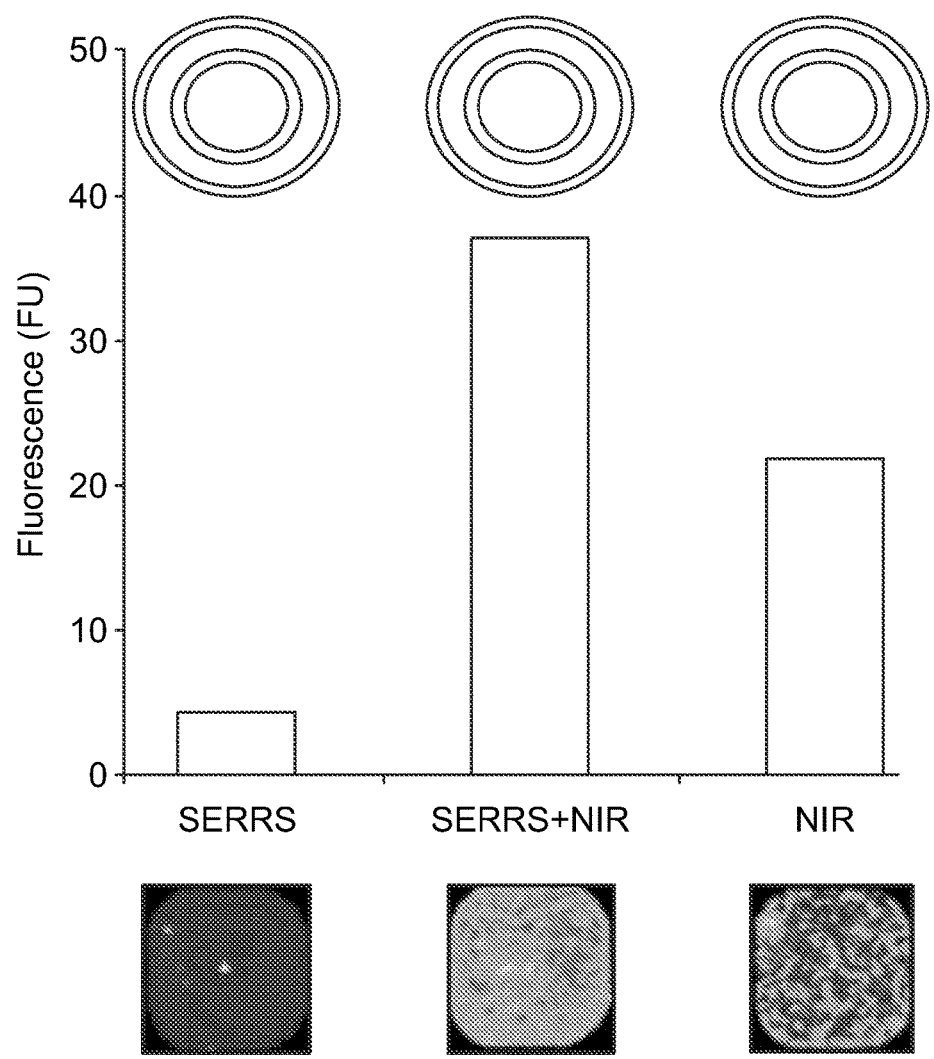
FIG. 17 illustrates a plot of exemplary particles versus their fluorescence intensities together with a series of fluorescence images, according to some embodiments of the present invention.

The exemplary particles used in this Example were synthesized as described in Example 4. In FIG. 17, it is demonstrated how the addition of a near infrared (NIR) fluorescent layer markedly increases the (NIR) fluorescent properties of the SERRS particles. This allows the use of these multilayered particles for the macroscopic delineation of the bulk tumor in the surgical bed.

Figure 18:
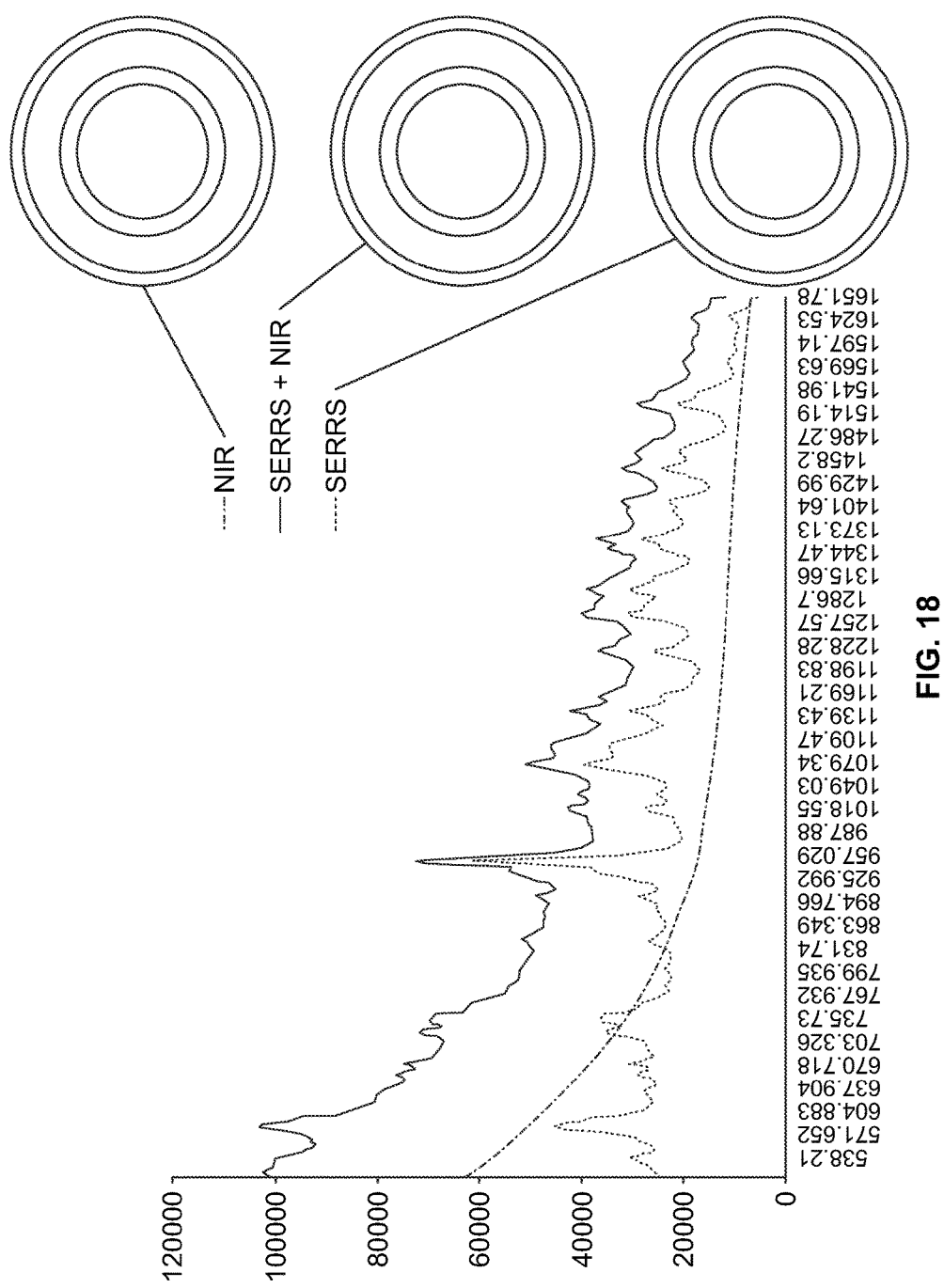
FIG. 18 shows Raman spectra of exemplary particles, according to some embodiments of the present invention.

As shown in FIG. 18, the signal intensity from the SERRS-layer (green) is not affected by the addition of a (near infrared) fluorescence layer (red) as indicated by the Raman spectrum (magenta) of the multimodal particle (middle). Since Raman can be used to detect microscopic lesions, this nanoparticle can be used to identify residual microscopic tumor deposits in the surgical bed after bulk tumor resection.

Figure 19:
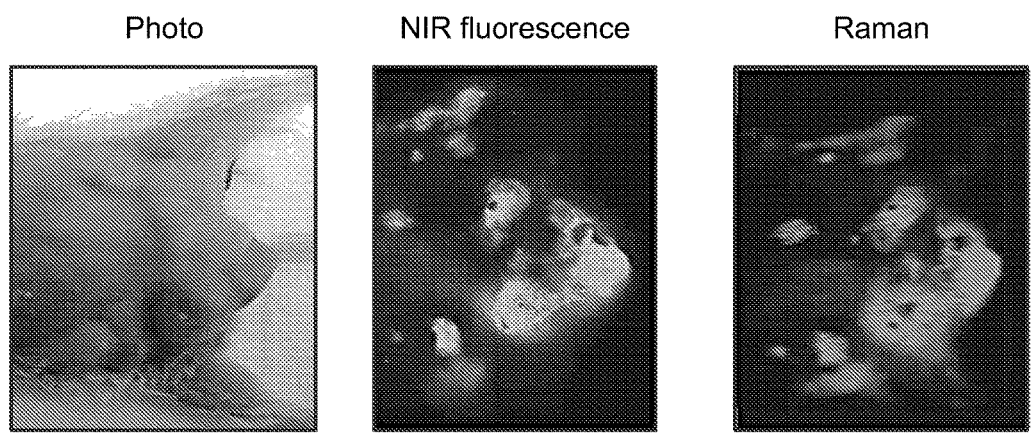
FIG. 19 shows images of an in vivo experiment using exemplary particles, according to some embodiments of the present invention.

FIG. 19 shows an in vivo experiment of a multimodal multilayer SERS and Fluorescent nanoparticle 24 h after i.v. injection in a breast cancer mouse model (PyMT), illustrating that the tumors are visualized with both modalities.

Other Embodiments and Equivalents

Those skilled in the art will recognize, or be able to ascertain using no more than routine experimentation, many equivalents to the specific embodiments of the invention described herein. The scope of the present invention is not intended to be limited to the above Description, but rather is as set forth in the following claims.

What is claimed is:

1. A composition comprising at least one particle comprised of:
   a nanoscale metal or metal alloy substrate;
   a first condensation layer that extends a distance from the nanoscale metal or metal alloy substrate, wherein the distance is up to 10 nm, and wherein the first condensation layer comprises a first dopant entity that is or comprises a SE(R)RS-active agent; and
   a second condensation layer comprising a second dopant entity, wherein the second dopant entity is a detectable entity selected from the group consisting of fluorochromes, MM agents, photoacoustic-active dyes, upconverting materials, positron emission tomography (PET) tracers, single photon emission tomography (SPECT) tracers, computed tomography (CT) agents, X-ray agents, ultrasound (US) agents, and combinations thereof so that the first dopant entity and the second dopant entity are detectable by different imaging modalities.

2. The composition of claim 1, wherein the second condensation layer has a thickness within the range of about 0.5 nm to about 5 μm and/or wherein the first dopant entity is positioned within 5 nm, or 10 nm of the surface of the nanoscale metal or metal alloy substrate.

3. The composition of claim 1, wherein the first condensation layer and/or the second condensation layer comprise(s) a material selected from the group consisting of metal, semi-metal, non-metal, oxides, borides, carbides, sulfides and nitrides of the metal, semi-metal or non-metal, oligomers, polypeptides, polymers and combinations thereof.

4. The composition of claim 3, wherein the metal, semi-metal or non-metal is or comprises silica, titania, zirconia, germania, alumina, tantalum pentoxide, or any combinations thereof.

5. The composition of claim 1, wherein the first condensation layer and the second condensation layer are comprised of a same material and/or wherein the first condensation layer and/or the second condensation layer comprise(s) silica layers.

6. The composition of claim 3, wherein the first condensation layer and/or the second condensation layer comprise(s) oligomers, polypeptides, polymers, or any combination thereof.

7. The composition of claim 1, wherein the second dopant entity is a NIR fluorescent agent.

8. The composition of claim 7, further comprising a third dopant entity.

9. The composition of claim 1, further comprising a buffer layer positioned between the first condensation layer and the second condensation layer, wherein the buffer layer lacks a dopant entity.

10. The composition of claim 1, wherein each of the first dopant entity and the second dopant entity is directly associated within each of the first condensation layer and the second condensation layer.

11. The composition of claim 1, wherein each of the first dopant entity and the second dopant entity is indirectly associated within each of the first condensation layer and the second condensation layer via a linker, or a chelator.

12. The composition of claim 1, wherein the nanoscale metal or metal alloy substrate is spherical.

13. The composition claim 1, wherein the nanoscale metal or metal alloy substrate is non-spherical.

14. The composition of claim 1, wherein the nanoscale metal or metal alloy substrate is or comprises a material selected from the group consisting of metals, metal oxides, liposomes, upconverting materials, semiconductors, and combinations thereof.

15. The composition of claim 14, wherein the metal is selected from the group consisting of gold, silver, copper, or any other material capable of sustaining localized surface plasmon resonance, and combinations thereof.

16. The composition of claim 1, wherein the nanoscale metal or metal alloy substrate is associated with surface primers and/or with capping agent entities.

17. The composition of claim 1, wherein the at least one particle is substantially free of surface primers.

18. The composition of claim 1, wherein the at least one particle has a diameter of about 5 nm to about 1000 nm or about 5 nm to about 200 nm.

19. A method of preparing a particle, comprising:

combining a first precursor solution of a first condensation layer in water and alcohol with a first dopant entity;

combining the first precursor solution with a nanoscale metal or metal alloy substrate under conditions and for a time necessary and sufficient to apply onto the nanoscale metal or metal alloy substrate the first condensation layer, which first condensation layer extends a distance from the nanoscale metal or metal alloy substrate which is up to 10 nm, resulting in a particle;

combining a second precursor solution of a second condensation layer in water and alcohol with a second dopant entity;

combining the second precursor solution with the particle under conditions and for a time necessary and sufficient to apply onto the particle the second condensation layer, which second condensation layer has a second predetermined thickness;

wherein the first dopant entity is or comprises a SE(R)RS-active agent, and wherein the second dopant entity is a detectable entity selected from the group consisting of fluorochromes, MRI agents, photoacoustic-active dyes, upconverting materials, positron emission tomography (PET) tracers, single photon emission tomography (SPECT) tracers, computed tomography (CT) agents, X-ray agents, ultrasound (US) agents, and combinations thereof so that the first dopant entity and the second dopant entity are detectable by different imaging modalities.

20. The method of claim 19, wherein the nanoscale metal or metal alloy substrate further comprises at least one layer.

21. A method comprising a step of providing to a site of interest a collection of particles each comprised of:

a nanoscale metal or metal alloy substrate;

a first condensation layer that extends a distance from the nanoscale metal or metal alloy substrate, wherein the distance is up to 10 nm, and wherein the first condensation layer comprises a first dopant entity that is or comprises a SE(R)RS-active agent; and a second condensation layer comprising a second dopant entity, wherein the second dopant entity is a detectable entity selected from the group consisting of fluorochromes, MRI agents, photoacoustic-active dyes, upconverting materials, positron emission tomography (PET) tracers, single photon emission tomography (SPECT) tracers, computed tomography (CT) agents, X-ray agents, ultrasound (US) agents, and combinations thereof so that the first dopant entity and the second dopant entity are detectable by different imaging modalities.

22. The method of claim 21, wherein the site of interest is or comprises a solid tumor and wherein the step of providing comprises administering the collection of particles to a location and in an amount such that particles from the collection of the particles localize to the solid tumor.

23. The method of claim 21, wherein the particles further comprise a targeting entity; and/or wherein the nanoscale metal or metal alloy substrate is gold; and/or wherein the second dopant entity comprises an entity selected from the group consisting of radionuclides, fluorescent dyes, and combinations thereof.

24. The method of claim 21, wherein the second dopant entity is a NIR fluorescent agent.

25. The method of claim 21, further comprising a step or a plurality of steps of imaging administered particles.

26. The method of claim 25, wherein different imaging modalities are utilized in different imaging steps and wherein different imaging steps utilizing different imaging modalities are performed substantially simultaneously.

27. The method of claim 25, wherein each imaging step of the plurality of imaging steps comprises utilizing an imaging modality selected from the group consisting of MRI, PET, SPECT, CT, X-ray, ultrasound, photoacoustic detection, fluorescent/Raman spectroscopy, and combinations thereof.

28. The method of claim 21, wherein the second dopant entity comprises an entity selected from the group consisting of radionuclides, fluorescent dyes, and combinations thereof, the method further comprising a first step of imaging administered particles, wherein the radionuclide generates Cerenkov signal.

29. The method of claim 28, further comprising a second step of imaging administered particles, wherein the radionuclide causes secondary Cerenkov induced fluorescence.

* * * * *

UNITED STATES PATENT AND TRADEMARK OFFICE
CERTIFICATE OF CORRECTION

PATENT NO. : 10,105,456 B2  
APPLICATION NO. : 14/653177  
DATED : October 23, 2018  
INVENTOR(S) : Stefan Harmsen, Matthew Wall and Moritz Kircher Page 1 of 1

It is certified that error appears in the above-identified patent and that said Letters Patent is hereby corrected as shown below:

In the Claims

Column 28, Line 15 Claim 1, delete "MM agents" after "chromes," and insert --MRI agents-- therefore.

Column 29, Line 7 Claim 15, delete "or" after "copper,".

Column 30, Line 34 Claim 26, insert --the-- after "wherein".

Column 30, Line 36 Claim 26, insert --the-- after "wherein".

Column 30, Line 47 Claim 28, insert --wherein-- after "thereof,".

Column 30, Line 47 Claim 28, delete "comprising" after "the method further" and insert --comprises-- therefore.

Column 30, Line 48 Claim 28, insert --and-- after "administered particles,".

Signed and Sealed this  
Nineteenth Day of February, 2019

Andrei Iancu  
*Director of the United States Patent and Trademark Office*